(12) United States Patent
Leong et al.

(10) Patent No.: US 7,841,446 B2
(45) Date of Patent: Nov. 30, 2010

(54) BANDLESS HEARING PROTECTOR AND METHOD

(75) Inventors: Waihong Leong, Roswell, GA (US); Steven Craig Gehling, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 187 days.

(21) Appl. No.: 12/215,485

(22) Filed: Jun. 26, 2008

(65) Prior Publication Data

US 2009/0095566 A1      Apr. 16, 2009

Related U.S. Application Data

(63) Continuation-in-part of application No. 11/799,264, filed on Apr. 30, 2007, now Pat. No. 7,648,005, and a continuation-in-part of application No. 11/821,391, filed on Jun. 22, 2007.

(51) Int. Cl.
  *H04R 25/02* (2006.01)
  *A61F 11/08* (2006.01)
  *H04R 25/00* (2006.01)
  *A61F 11/06* (2006.01)

(52) U.S. Cl. .................. 181/135; 181/130; 381/328; 381/330; 381/374; 381/380; 128/867

(58) Field of Classification Search ............... 181/135, 181/130, 129, 131; 381/328, 329, 330, 72, 381/23.1, 381, 374, 380; 128/864, 866, 867
See application file for complete search history.

(56) References Cited

U.S. PATENT DOCUMENTS 466,725 A   1/1892   Miltimore

| | | | |
|---|---|---|---|
| 1,576,938 A | 3/1926 | Struxiano | |
| 1,668,890 A | 5/1928 | Curran et al. | |
| 1,668,910 A * | 5/1928 | Jones | 181/130 |

(Continued)

FOREIGN PATENT DOCUMENTS

FR      2 157 177 A5      6/1973

(Continued)

OTHER PUBLICATIONS

American National Standard, ANSI S3.19/1974 (R 1979) (ASA Jan. 1975), "Method for the Measurement of Real-Ear Protection of Hearing Protectors and Physical Attenuation of Ear Muffs," published by the Acoustical Society of America, pp. 1-9.

(Continued)

*Primary Examiner*—Edgardo San Martin
(74) *Attorney, Agent, or Firm*—Denise L. Stoker

(57)      ABSTRACT

A hearing protection device and method of use intended for a human ear. A plug member caps or enters ear canal, and may be shaped to conform to the external auditory meatus. The plug member may be part of a replacement assembly. The device is biased at least in part by a pressure pad to provide some force against the plug member. An optional handle may be provided to assist with temporarily pulling the plug member away from the ear canal or providing adjustment. An optional bow member clips about the pinna. The device may be adapted for use as an ear phone.

21 Claims, 23 Drawing Sheets

U.S. PATENT DOCUMENTS

| | | | |
|---|---|---|---|
| 1,893,143 A * | 1/1933 | Koch | 181/135 |
| 1,953,437 A * | 4/1934 | Schier | 181/135 |
| 2,487,038 A | 11/1949 | Baum | |
| 2,939,923 A | 6/1960 | Henderson | |
| 3,041,856 A * | 7/1962 | Neal | 63/14.1 |
| 3,431,370 A * | 3/1969 | Crosby | 181/131 |
| 3,667,569 A | 6/1972 | Mackey et al. | |
| 3,682,268 A | 8/1972 | Gorike | |
| 3,783,201 A | 1/1974 | Weiss et al. | |
| 3,915,166 A | 10/1975 | McCrink | |
| D245,202 S * | 7/1977 | Asker | D24/106 |
| RE29,487 E | 12/1977 | Gardner, Jr. | |
| 4,223,189 A | 9/1980 | Warren | |
| 4,490,857 A | 1/1985 | Leight et al. | |
| 4,819,624 A * | 4/1989 | Leight et al. | 128/866 |
| 5,420,381 A | 5/1995 | Gardner, Jr. et al. | |
| 5,450,496 A | 9/1995 | Burris et al. | |
| 5,712,453 A * | 1/1998 | Bungardt et al. | 181/135 |
| 5,761,298 A * | 6/1998 | Davis et al. | 379/430 |
| 5,824,966 A | 10/1998 | Leight | |
| 5,953,435 A * | 9/1999 | Mullin et al. | 381/380 |
| 6,038,329 A | 3/2000 | Lee | |
| 6,056,082 A * | 5/2000 | Lindgren et al. | 181/130 |
| 6,105,714 A | 8/2000 | Lindgren | |
| 6,122,388 A * | 9/2000 | Feldman | 381/322 |
| 6,394,947 B1 | 5/2002 | Leysieffer | |
| 6,728,388 B1 | 4/2004 | Nageno et al. | |
| 6,751,331 B2 | 6/2004 | Eisenbraun | |
| 6,785,396 B2 | 8/2004 | Shirata | |
| 6,804,364 B1 | 10/2004 | De Jonge | |
| 6,810,987 B1 | 11/2004 | DeKalb | |
| 6,819,772 B2 | 11/2004 | Amae | |
| 7,011,087 B1 | 3/2006 | Sullivan | |
| 7,031,485 B2 * | 4/2006 | Webber et al. | 381/380 |
| 2002/0131585 A1 * | 9/2002 | Jones et al. | 379/431 |
| 2002/0172386 A1 * | 11/2002 | Bayer | 381/330 |
| 2003/0044038 A1 | 3/2003 | Shirata | |
| 2003/0112992 A1 | 6/2003 | Rapps | |
| 2003/0174853 A1 * | 9/2003 | Howes et al. | 381/370 |
| 2003/0196850 A1 * | 10/2003 | Dyer et al. | 181/135 |
| 2004/0096075 A1 * | 5/2004 | Kuhlmann et al. | 381/312 |
| 2004/0170294 A1 | 9/2004 | Murozaki et al. | |
| 2005/0002539 A1 | 1/2005 | Nielsen | |
| 2005/0069145 A1 * | 3/2005 | Sjoqvist | 381/72 |
| 2005/0271228 A1 | 12/2005 | Lai et al. | |
| 2006/0198544 A1 | 9/2006 | Yueh | |
| 2006/0215864 A1 | 9/2006 | Espersen et al. | |
| 2007/0010704 A1 | 1/2007 | Pitulia | |
| 2008/0037817 A1 | 2/2008 | Ewert et al. | |
| 2008/0137897 A1 | 6/2008 | Liu | |
| 2008/0144877 A1 | 6/2008 | Ham et al. | |
| 2008/0181441 A1 * | 7/2008 | Smith | 381/328 |
| 2008/0264429 A1 | 10/2008 | Leong et al. | |
| 2008/0264715 A1 | 10/2008 | Leong et al. | |
| 2009/0245556 A1 * | 10/2009 | Parker et al. | 381/326 |
| 2010/0166204 A1 * | 7/2010 | Yanagishita et al. | 381/375 |

FOREIGN PATENT DOCUMENTS

| | | |
|---|---|---|
| FR | 2 558 055 A1 | 7/1985 |
| GB | 191504579 A | 2/1916 |
| GB | 0 258 280 A | 2/1927 |
| GB | 0 833 506 A | 4/1960 |
| GB | 2 374 684 A | 10/2002 |
| GB | 2 375 967 A | 12/2002 |
| GB | 2 407 513 A | 5/2005 |
| JP | 2000165972 A * | 6/2000 |

OTHER PUBLICATIONS

American Society for Testing Materials (ASTM) Designation: D 570-98 (Reapproved 2005), "Standard Test Method for Water Absorption of Plastics," pp. 1-4, published Jan. 2006.

American Society for Testing Materials (ASTM) Designation: D2240-05, "Standard Test Method for Rubber Property—Durometer Hardness," pp. 1-13, published Sep. 2005.

American Society for Testing Materials (ASTM) Designation: D2856-94, "Standard Test Method for Open-Cell Content of Rigid Cellular Plastics by the Air Pycnometer," pp. 143-148, published May 1994.

American Society for Testing Materials (ASTM) Designation: D3574-05, "Standard Test Methods for Flexible Cellular Materials—Slab, Bonded, and Molded Urethane Foams," pp. 1-25, published Aug. 2005.

"Koss Titanium Earclips with Volume Control," sold by RadioShack® on Internet web page "http://www.radioshack.com/sm-koss-titanium-earclips-with-volume-control—pi-2206192.html" viewed and printed Apr. 6, 2007, pp. 1-2.

"Quiet Pro®," Internet web page "http://www.nacre.no/", Nacre®, Trondheim, Norway, viewed and printed Jun. 21, 2007, 1 page.

Patent Cooperation Treaty Search Report from the International Search Authority, International Application No. PCT/IB2009/052582 dated Feb. 11, 2010.

* cited by examiner

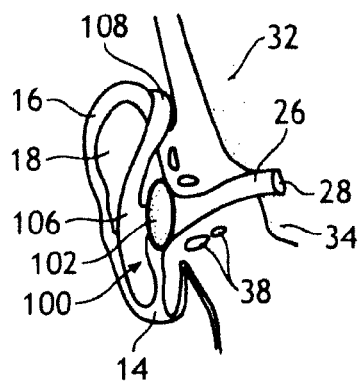 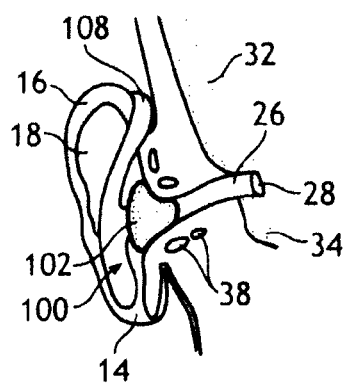 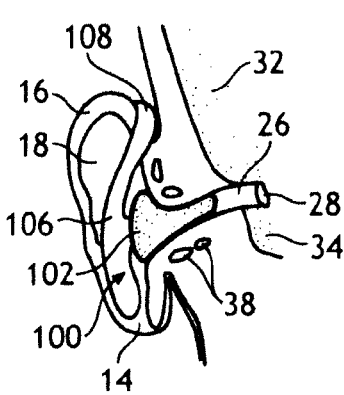
FIG. 3　　　　FIG. 4　　　　FIG. 5
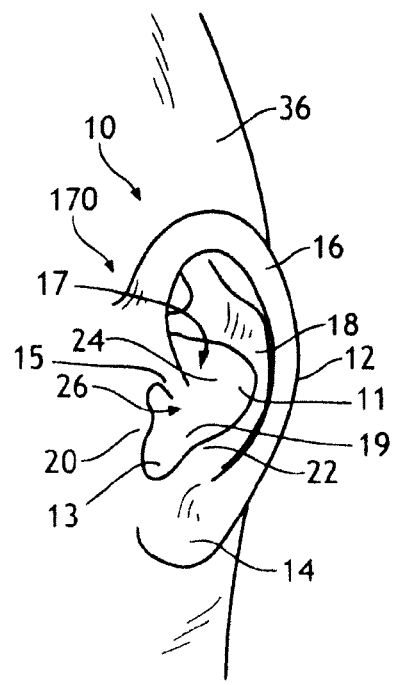 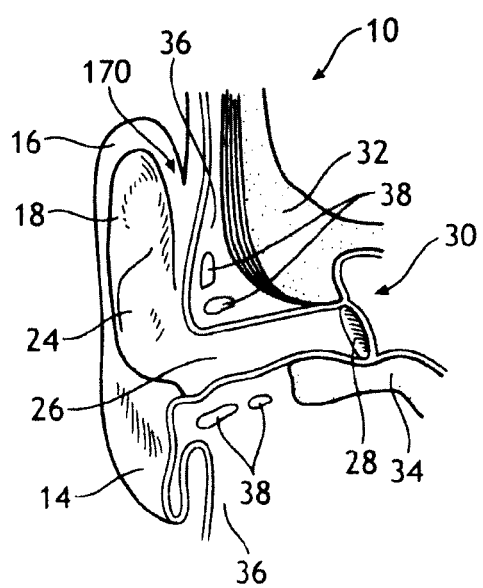
FIG. 1　　　　FIG. 2

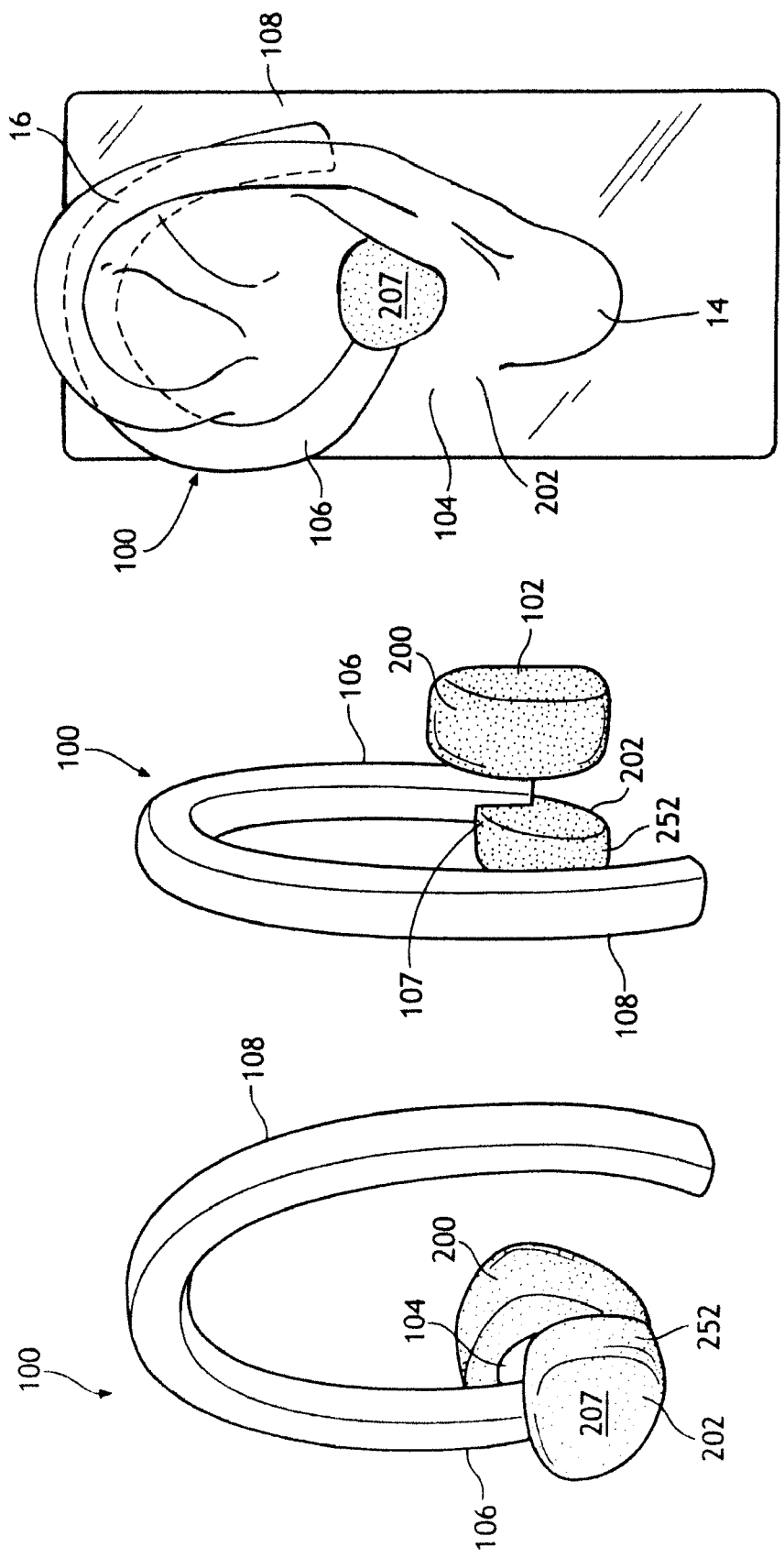

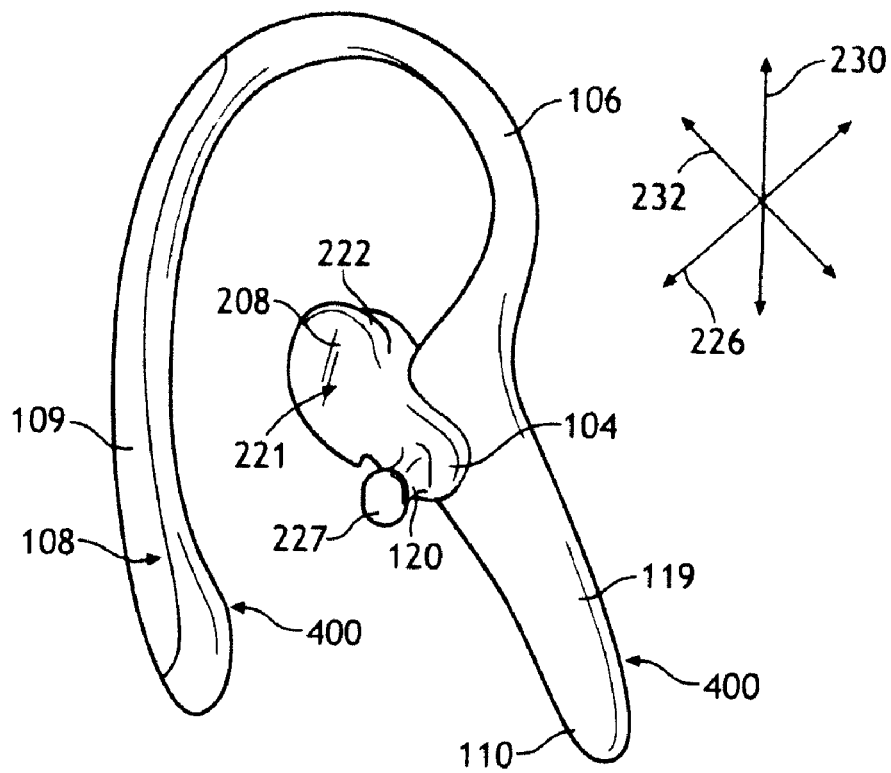
FIG. 20
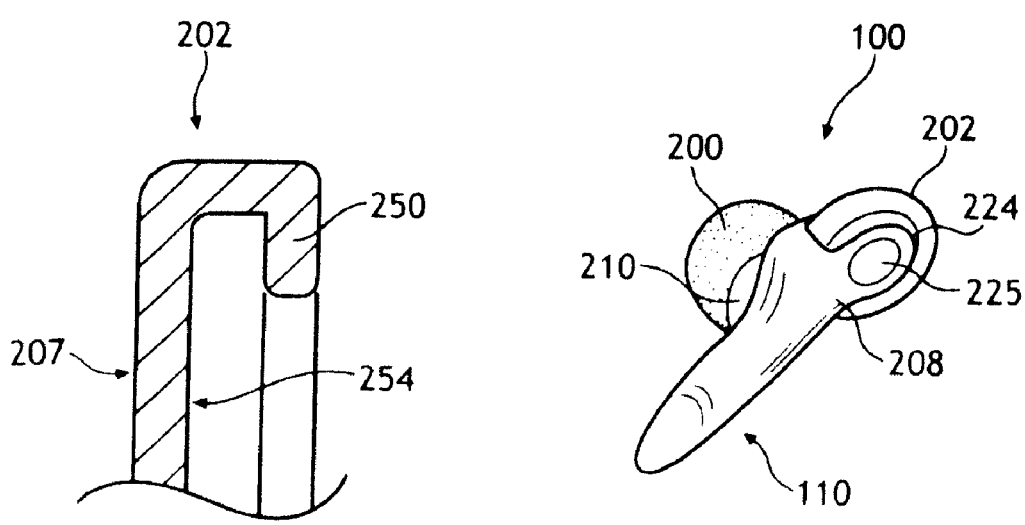
FIG. 20A  FIG. 21

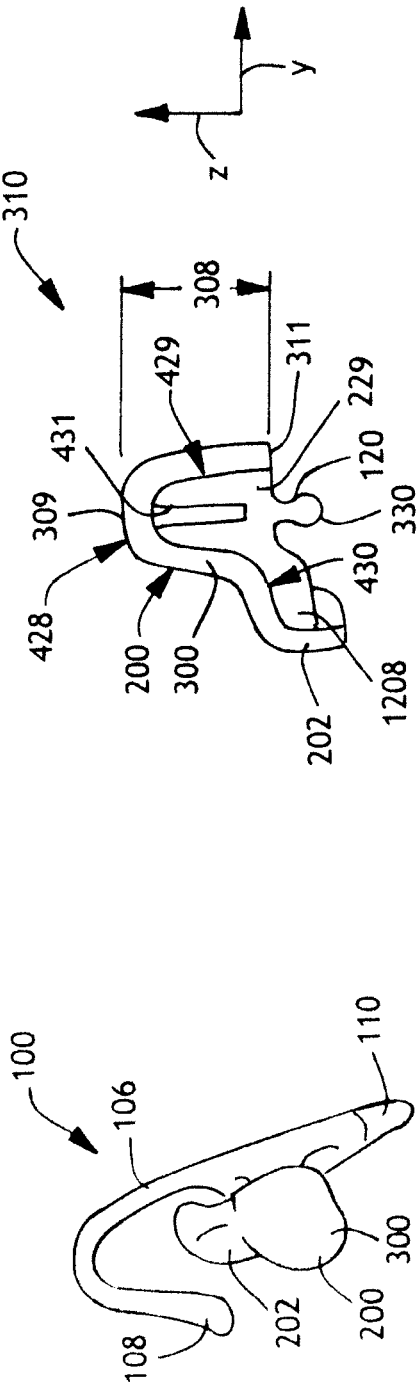
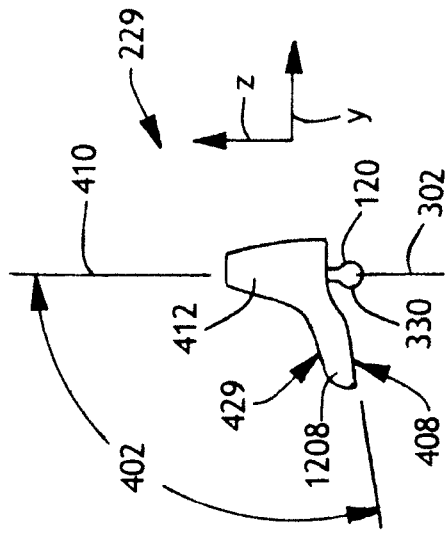
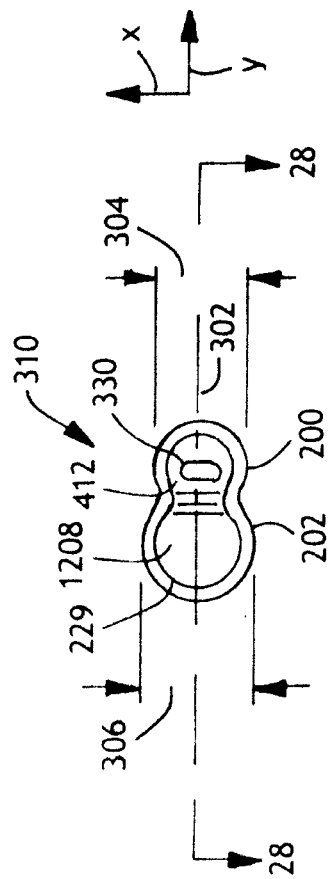
FIG. 28
FIG. 31
FIG. 27
FIG. 30

BANDLESS HEARING PROTECTOR AND METHOD

This application is a continuation-in-part of application Ser. No. 11/799,264 filed Nov. 30, 2007 now U.S. Pat. No. 7,648,005, and application Ser. No. 11/821,391 filed on Jun. 22, 2007.

BACKGROUND OF THE INVENTION

High level sound vibrations and perhaps particularly the steady recurring sounds or din in industrial operations are known to cause traumatic hearing impairments and even loss of hearing. Often these types of impairments do not respond to hearing aids or surgery. As would be expected, there are numerous types of hearing protectors for noise deadening or noise reduction.

One type of conventional hearing protection device are foam ear plugs that may be compressed and inserted into the ear, and then allowed to expand to fit the ear canal. While these types of ear plugs may be useful, they can be uncomfortable and difficult to insert correctly. Furthermore, handling ear plugs to compress, remove or replace may be unsanitary.

Another type of conventional hearing protection device includes a U-shaped headband having an inwardly directed ear plug affixed to each of the opposed ends. While it is easy and more sanitary to temporarily pull an ear plug away from the ear, the conventional headband may have certain drawbacks and deficiencies.

For some persons, ear bands can cause pressure and are uncomfortable to wear for long periods of time. The headband can be shaped such that portions of the headband may be close to or touching the wearer's head, and can become irritating and uncomfortable to the wearer. In addition, there is no mechanism for adjusting the headband to allow for varying head sizes. A wearer with a large head requires a large distance between the headband ends on which the ear plugs are attached. Unfortunately, as the distance between the headband end increases, so does the tension in the headband. Accordingly, wearers with relatively large heads may experience discomfort due to this high tension in the headband.

In light of the foregoing problems and issues discussed above, it is desirable to have a hearing protection device that can comfortably fit a wide variety of users. It is also desirable to have a hearing protection device that may be temporarily moved away from the ear without contamination by the hand.

SUMMARY OF THE INVENTION

In one aspect of the present invention, there is a hearing protection device for the passive attenuation of sound at a single human ear canal, the device including a replacement assembly with an EAM pad that is integrally connected to a pressure pad, and a support frame. A positioning member assists with disposing the hearing protection device into the ear canal.

In another aspect of the invention is a system for providing passive hearing protection to a population. The system includes a first replacement assembly and a second replacement assembly, each having an EAM pad, a pressure pad, and a support frame. The system also includes a positioning member for locating the hearing protection device into the ear canal. The first replacement assembly has an EAM pad having a first configuration, and the second replacement assembly comprises an EAM pad having a different and second configuration. The first replacement assembly and the second replacement assembly are each attachable to the positioning member.

In yet another aspect of the present invention is a method of positioning a passive hearing protection device on a wearer with respect to a human ear. The hearing protection device includes an EAM pad connected to a pressure pad to form a replacement pad. The replacement pad is supported by a support frame, and the support frame member is selectively attached to a positioning member. The method includes the following steps: locate structures of the wearer's ear, the structures comprising a pinna and an ear canal opening, wherein the ear canal opening is adjacent to other ear structures and regions including a concha and an antitragus; pull the pinna toward a top region of the wearer's head; position the EAM pad over the ear canal opening; push the EAM pad toward the ear canal opening; and wedge the pressure pad between the concha and the antitragus.

In a further aspect of the present invention there is a passive hearing protection device adapted to fit a human ear canal. This device includes a plug member adapted to cover or enter the human ear canal, wherein the plug member is attached to a positioning member.

A pressure pad is attached to the positioning member or the plug member; the pressure pad is adapted to fit between into a cavum concha region of the human ear.

The positioning member is makes contact with an ear structure near the human ear canal to limit how far the plug member may enter into the human ear canal when the hearing protection device is positioned to effectively attenuate sound in the human ear to a desired attenuation level.

Other features of the invention will be in part apparent and in part pointed out hereinafter as well as better understood by practice of the invention. It is to be understood that both the foregoing general description and the following detailed description are exemplary and are intended to provide further explanation of the invention claimed. The accompanying drawings, which are incorporated in and constitute part of this specification, are included to illustrate and provide a further understanding of the bandless hearing protection device that is the present invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 1 is a side view of a human ear, illustrated to provide context for the present invention.

FIG. 2 is a front partial cross-section of a human ear, illustrated to provide context for the present invention.

FIG. 3 is the human ear as shown in FIG. 2, with one embodiment of the hearing protector of the present invention disposed on the ear, showing a plug member that covers the ear canal entrance.

FIG. 4 is the human ear as shown in FIG. 2, with a second embodiment of the hearing protector of the present invention disposed on the ear, showing a plug member that partially enters the ear canal.

FIG. 5 is the human ear as shown in FIG. 2, with a third embodiment of the hearing protector of the present invention disposed on the ear, showing a plug member that fully enters the ear canal.

FIG. 13A is a side perspective view of another embodiment of the hearing protector of the present invention, showing a pressure pad.

FIG. 13B is a rear perspective view of the hearing protector shown in FIG. 13A.

FIG. 14 is a side perspective view of yet another embodiment of the hearing protector of the present invention as it would appear when engaging an ear.

FIG. 20 is a partial perspective view of the hearing protector shown in FIG. 18, minus the pressure pad and the EAM pad.

FIG. 20A a partial cross-section of the pressure pad taken at lines 20A-20A of FIG. 19.

FIG. 21 is side perspective view of the eighth embodiment of a hearing protector of the present invention.

FIG. 27 is a front perspective view of the left-side version of the hearing protector of FIG. 26A, in a fully assembled condition.

FIG. 28 is a cross-sectional side view of the replacement assembly shown in FIG. 27, taken at line 28-28 at FIG. 30.

FIG. 30 is a bottom plan view of the replacement assembly shown in FIG. 27.

FIG. 31 is a side elevation of the support frame member shown in FIG. 28.

DETAILED DESCRIPTION OF THE PRESENT INVENTION

Figure 6:
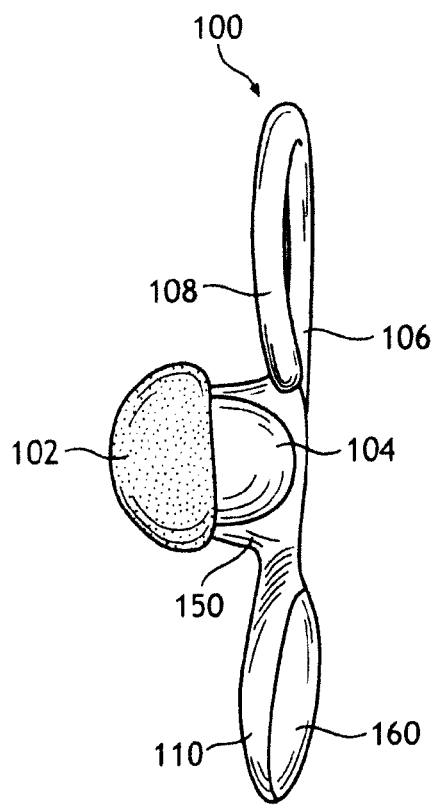
FIG. 6 is a front elevation view of a fourth embodiment of the hearing protector of the present invention, shown in a biased state.

The present invention is a hearing protector for the human ear 10. In order to provide context for the present invention, a brief discussion of human ear anatomy is presented. Referring to FIG. 1, the externally visible anatomy of the human ear 10 is largely defined by the pinna 12. The pinna 12 has various contours and folds which aid hearing, such as the lobe 14, helix 16, anti-helix 18, tragus 20, and anti-tragus 22. The concha 24 is an indented region roughly defined by the anti-helix 18, tragus 20, and anti-tragus 22. There are additional regions within the concha 24. A region called the back concha 11 is located adjacent the anti-helix, and a region called the front concha 13 is located between the tragus 20 and the anti-tragus 22. The concha is further divided by a crus helis 15. The region above the crus helis 15 is the cymba concha 17, and the region below, the cavum concha 19. In the concha 24 region, one will find the opening to the ear canal 26.

Referring now to FIG. 2, the interior of the ear is shown. In particular, the ear canal 26 is an elongated channel that terminates at the ear drum 28. Beyond the ear drum 28 is a region known as the middle ear 30. The ear drum 28 and the section of ear canal 26 in closest proximity thereto is located between two bony parts of skull, namely the temporal bone 32 and the occipital bone 34. Such bony parts, along with the entire skull, are covered by flesh and adipose material, generically referred to as tissue 36. The pinna 12 is connected to the tissue 36. The pinna 12 stiffness and shape is defined by cartilage 38, seen in cross-section in FIG. 2.

The present invention is a hearing protector 100 (FIG. 6) that clips to the pinna 12. The hearing protector may be unitary in construction, or assembled from two or more separate parts. Further, the hearing protector 100 will have a left or right orientation, depending on whether it is adaptable for the left or right ear. Regardless of the number of parts or the orientation of hearing protector 100, each embodiment of the present invention has several general sections. For instance, as seen in the embodiment shown in FIGS. 6-7, there is a plug 102 connected to a neck 104. Plug 102 is a pliable member that may conform to a portion of the ear canal 26, or at least the entrance of the ear canal at concha 24. An "ear clip" is defined by a neck 104 that extends from a shoulder 106, and which is connected to an arm 108. Together, the shoulder 106 and arm 108 form a "bow member" that generally extends from the tragus 20, upward to where helix 16 meets tissue 36, and down around the pinna 12 adjacent to where concha 24 meets tissue 36. The arm 108 may further wrap around and contact the lobe 14. The bow member may be biased such that when the hearing protector is clipped to the pinna 12, pressure is applied to the neck 104, forcing the plug 102 toward ear canal 26. Thus, the neck 104 is a "pressure member." Details of the various embodiments of the present invention are described below.

Hearing protectors 100 fall generally into three categories, including protectors that cover the entrance to ear canal 26 (referred to as cap devices) (FIG. 3), protectors which partially enter and seal ear canal 26 between the sections of ear cartilage 38 (referred to as semi-insert devices) (FIG. 4), and protectors that enter the ear canal and extend further toward the ear drum even with or just past the ear cartilage 38 (referred to as full-insert devices) (FIG. 5).

Hearing protectors 100 which enter the ear canal to a greater degree offer better protection against harmful noise levels because vibrations from the ear cartilage and ear canal tissue is attenuated, and the ear canal is at least partially sealed against the noisy environment. However, full-insert and even semi-insert devices may be less comfortable than those which simply cap the ear canal 26. Typically, plugs 102 that cap the ear canal 26 are used for intermittent noise exposures where lighter weight and improved low frequency attenuation are desirable. As used herein, "hearing protectors" refers generally to hearing protectors falling into one of the three categories described above. For reasons of simplicity, the embodiments of the present invention illustrated in FIGS. 6-25 include plugs 102 that operate as cap devices. However, it should be understood that the plugs 102 could be enlarged such that they operate as semi-insert or full-insert devices as shown in FIGS. 4 and 5, respectively.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

Figure 7:
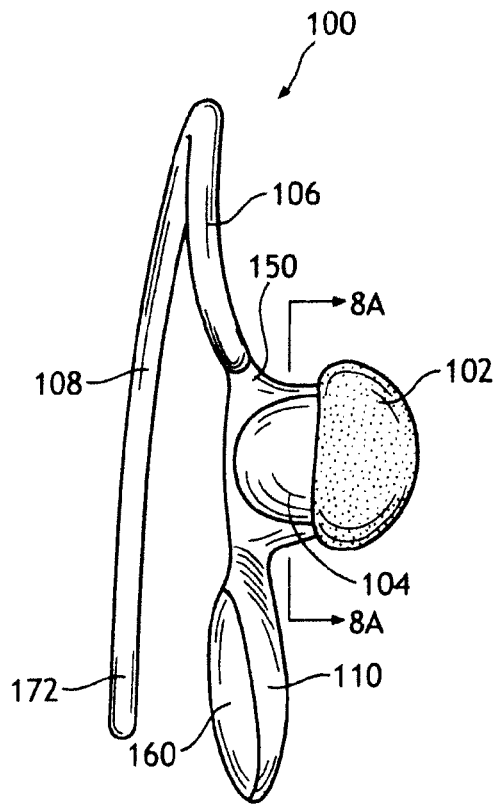
FIG. 7 is a front elevation view of the hearing protector of FIG. 6, shown in an unbiased state.

As shown in FIGS. 6-7, a first embodiment of hearing protector 100 desirably has a unitary construction, with the possible exception of the plug 102. The neck 104, shoulder 106, handle 110, and arm 108 may be molded from a plastic material having the following characteristics: flexible enough to move the arm 108 to the backside of pinna 12 as neck 104 is positioned near the ear canal 26; durable enough to be used more than one time; moldable, as by injection molding or the like; and steady-state in that it does not exhibit significant loss of stiffness under a continuous load, allowing neck 104 and plug 102 to maintain an effective force toward the ear canal 26. Desirably, a material such as polyethylene is used. However, it is contemplated that the ear clip portion of hearing protector 100 may be manufactured from nylon, plastics such as polypropylene, polyvinyl chloride, polycarbonate; metals such as titanium, steel, or aluminum composites; or elastomer such as silicon, thermoplastic elastomer (TPE), polyurethane rubber, ethylene propylene rubber, or a combination thereof.

Referring to FIG. 7, a plug 102 is connected to the neck 104. The ear plug 102 may be a separate button of a flexible material as described below, shaped so that it sufficiently seats against the concha 24, tragus 20 and anti-tragus 22 surrounding the entrance to the ear canal 26. Plug 102, when functioning as a cap (FIG. 3) may be of a generally hemispherical shape and has a diameter somewhat greater than that of the average adult human ear canal, or another rounded shape.

For semi-insert or full-insert plugs (FIGS. 4-5), the plug 102 of the invention may be substantially cylindrical in shape and have at least a portion of the diameter somewhat greater than that of the average adult human ear canal. For instance, a diameter of between about 7 cm and about 15 cm is generally acceptable. Desirably, the diameter of the earplug will be between 8 cm and 14 cm. Further, it should be noted and understood that the term "cylindrical" as employed herein includes within its scope structures having a relatively shallow truncated cone shape or a substantially spherical shape. Where the earplug takes the form of a truncated cone, the above diameter criteria may be taken at the midpoint of the cone. Where the earplug is spheroid, the above criteria may be applied to the major diameter of said spheroid.

Plug 102 may be connected to neck 104 in a variety of ways. A first exemplary embodiment of a plug-neck connection, shown in FIG. 8B, has a stem 120 that is placed a corresponding cavity 122 in plug 102. This type of arrangement may allow the wearer to change only the plug 102, and reuse the remaining portion of the hearing protector 100. If the stem 120 is long enough to fit at least partially into the ear canal 26 (FIG. 4 or 5), the stem 104 is preferably flexible so that it moves and conforms to the irregularities of the ear as the wearer adjusts the hearing protective device. A non-pliable stem may cause discomfort as the wearer adjusts the hearing protection device. To provide a secure fit in the cavity 122, the stem 120 may be made from a compressible, resilient material and have a width dimension slightly larger than the width dimension of cavity 122; when the stem 120 is positioned in cavity 122, the stem 104 will press against the wall defining cavity 122 to provide a friction fit. It is further contemplated that a more permanent connection between stem 120 and plug 102 may be achieved with an adhesive. Adhesives such as hot-melt glue, cyanoacrylate glue, casein glue, cement glue, and resin glue would be suitable for this purpose.

Figure 8A:
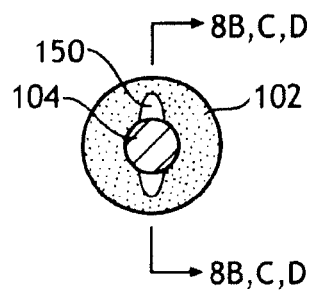
FIG. 8A is a partial cross section of the hearing protector of FIG. 7, taken at the plane defined by line 8A-8A.
Figure 8B:
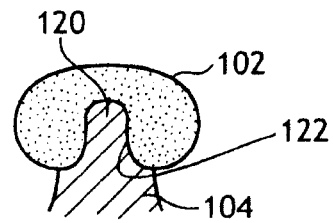
FIG. 8B is a partial cross-section of the hearing protector of FIG. 8A, showing one embodiment of the plug member attachment to the stem, and taken at the plane defined by line 8BCD-8BCD.
Figure 8C:
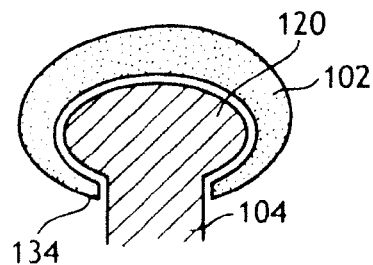
FIG. 8C is a partial cross-section of the hearing protector of FIG. 8A, showing one embodiment of the plug member attachment to the stem, and taken at the plane defined by line 8BCD-8BCD.

In a second exemplary embodiment of a plug-neck connection, shown in FIG. 8C, the neck 104 has a mushroom-shaped stem 130. A plug 102 having a corresponding mushroom-shaped cavity 132 therein is disposed over stem 130. Desirably, there is enough tension in the annulus 134 at the entrance of the cavity 132 to keep the plug 102 from slipping off of the stem 130 as the hearing protector is adjusted within or removed from the ear.

Figure 8D:
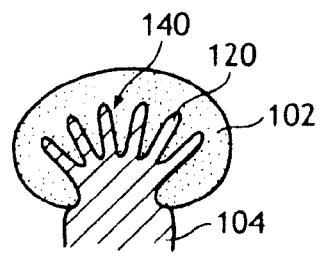
FIG. 8D is a partial cross-section of the hearing protector of FIG. 8A, showing one embodiment of the plug member attachment to the stem, and taken at the plane defined by line 8BCD-8BCD.

In a third exemplary embodiment of a plug-neck connection, shown in FIG. 8D, the neck 104 has a flanged end 140. A plug 102 is adhesively connected to the flanged end 140 by an adhesive as previously described for the stem of FIG. 8B and/or a mechanical connection.

It is to be understood that the particular compound for making plug 102 is less important than the mechanical qualities of the plug 102. Most desirably, the earplug, when deformed, will tend to recover its original shape and size. The conformity of the foamed polymeric composition will create a seal against the ear wall to block sound from entering into ear canal. The principal characteristics exhibited by the ear plug material are that it is soft and pliable to conform to the shape of the ear canal and ear canal entrance.

In one embodiment, the plug 102 material may have a skin formed on its outer surface, with the skin broken to permit the venting of the ear canal (not shown). With the open-cell construction of the plug 102, air may slowly escape from the ear canal to the surrounding atmosphere until the pressures are equalized. If the atmospheric pressure increases, the pressure within the ear canal may again be equalized to eliminate dizziness, vertigo, or other discomfort. It will be realized that the rate of flow of air through the open cell foam will be relatively slow and hence, the pressure equalization will not in any way affect the sound attenuating properties of the hearing protector 100.

In each of the exemplary embodiments described herein, the plug 102 may be made from dynamically stiff foam. One suitable dynamically stiff foam is described in U.S. Pat. No. 5,420,381, the contents of which are incorporated herein by reference to the extent they are consistent with the present invention. Alternatively, the plug 102 may comprise any other conventional earplug foam material such as the foam disclosed in U.S. Reissue Pat. No. 29,487, all of the contents of which are also incorporated herein by reference to the extent it is consistent with the present invention. In yet another embodiment, plug 102 may be made from elastomeric polymers such as silicon rubber. However, it is noted that any flexible polymeric material which can be foamed so as to result in a formed plug structure meeting the design criteria set forth herein constitutes a satisfactory material of construction in the plugs 102 of the invention. Accordingly, polymers of ethylene, propylene, vinyl chloride, vinyl acetate, diisocyanate, cellulose acetate or isobutylene can all be generally employed.

The neck 104 may have a solid cross-section as seen in FIG. 8A. Desirably, neck 104 is substantially cylindrical in shape, but may have other shapes that fit into the concha 24, between the tragus 20 and anti-tragus 22. A flange 150 may provide strength to the junction between the shoulder 106 or handle 110 and the neck 104. However, the precise shape of the neck and flange may be greatly influenced by aesthetic design, and it is contemplated that other shapes would be suitable, as evidenced by the other embodiments of hearing protector 100 described herein.

Shoulder 106 is a section of the hearing protector 100 that will experience relatively high stress as compared to the neck 104 and the arm 108. Shoulder 106, operates as the spring member of hearing protector 100. With respect to a reference plane that lies along line 8A-8A of FIG. 7, and 8BCD-8BCD of FIG. 8A, shoulder 106 operates to project arm 108 away from the reference plane. When the hearing protector 100 is clipped about the pinna 12, the arm 108 is forced in a direction toward the reference plane. In this regard, the shoulder 106 operates as a partial helical spring. The shoulder 106 is then under stress, and it too, may flex closer toward the reference plane. The hearing protector 100 appears more flattened which in use, and is in a stressed state (see FIG. 6). Shoulder 106 may have a curved appearance when viewed from the side, similar to the embodiment shown in FIG. 12. However, it is contemplated various other curvatures or aesthetic shapes may be incorporated into the shoulder 106 shape without affecting functionality.

Handle 110 (FIG. 17) is an optional feature that enables a user to conveniently grip the hearing protector 100 to manipulate the bow member for attachment to the ear. Handle 100 may also be used to temporarily pull the plug 102 away from the ear canal 26 or adjust the position of plug 102. Handle 110 is generally an elongated shape. However, as it is only used as a handle and may not experience as much stress as other sections of hearing protector 100, handle 110 may incorporate many aesthetic features without affecting its function. For example, a separate material 160 may be overlaid onto or otherwise attached to handle 110 to add visual interest and/or a different tactile feature. It is contemplated that handle 110 may be constructed from a unitary member.

Arm 108 is a flexible member that curves about pinna 12 from about junction 170 (where the helix 16 meets the head tissue 36) to the back of the pinna (see FIGS. 1 and 2). Desirably, the distal end 172 (FIG. 7) may hang down near the lobe 14, or even partially wrap around the concha 24. This configuration makes it easier to remove and replace the hearing protector 100 onto the ear. Also desirably, the distal end is rounded so as to increase comfort.

As mentioned previously, the neck 104, shoulder 106, and arm 108 may be constructed as a unitary piece, as by injection molding. However, it is contemplated that these regions could include one or more parts or over-molded pieces, similar to the embodiments of FIGS. 9-12, as discussed herein.

In operation, the device of FIGS. 6-7 is biased toward the ear so that the neck 104 will press the plug 102 inward toward a position capping the ear canal 26. To apply the hearing protector of FIG. 7, the arm 108 is placed behind the pinna 12 so that is rests against a portion of pinna 12 such as the concha 24, and the head tissue 36. The wearer disposes the plug 102 into or over the entrance of the ear canal 26. When the hearing protector is applied in this manner, it appears more flattened, as in FIG. 6. The neck 104 and plug 102, by bearing against the portion of the ear surrounding the entrance to the canal, reduces the amount of sound that is transmitted along the canal and also reduces the sound transmitted by the flesh and bone structure to the middle and inner ear. The hearing protector 100 shown FIG. 3, while aesthetically different, operates in the same manner.

Figure 9:
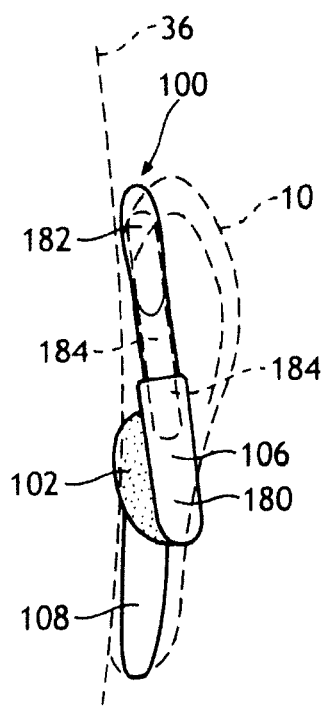
FIG. 9 is a front elevation view of a fifth embodiment of the hearing protector of the present invention, shown in a biased state as it engages an ear.
Figure 10:
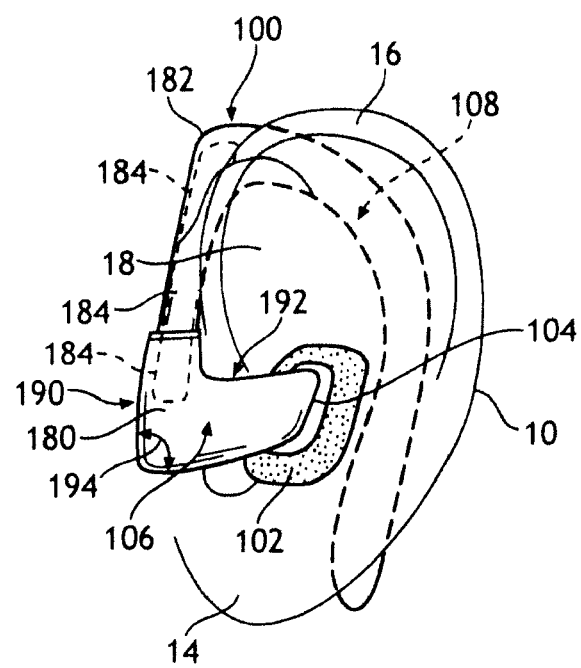
FIG. 10 is a side elevation view of the hearing protector of FIG. 9.

A second exemplary embodiment of the hearing protector 100, shown in FIGS. 9-10, is assembled from several separate parts. Generally, the hearing protector 100 of this embodiment operates the same way, but provides more opportunity for aesthetic enhancement and for optimizing strength properties in particular regions of hearing protector 100, such as the shoulder 106. This may provide opportunity to provide a higher performance hearing protector 100 at a lower cost. As can be seen, the overall shape of the hearing protector is more angular. This may be purely aesthetic, or be due to the use of a straight component, as described herein.

In this particular embodiment, a first component is the neck 104 and a portion of the shoulder 106, which collectively define an elbow 180. A second component is a spring 184, which is a member that functions as a torsion spring. A third component is the arm 108 and integrally-connected partial-sleeve 182. Sleeve 182 overlaps a portion of the shoulder region 106 where it connects to spring 184. Yet a fourth component is the plug 102, that attaches to the neck in the way described in the previous embodiment.

The neck 104 and shoulder 106 may be constructed from a molded plastic such as polyethylene, polypropylene, polyvinyl chloride, polycarbonate, and the like. Arm 108, along with integral sleeve 182, is desirably a flexible member manufactured from the same type of materials described for the embodiment shown in FIG. 6. The spring 184 may be constructed from various metals or composite materials, for example, spring steel.

Desirably, elbow 180 is an L-shaped member having a short leg 190 and a long leg 192. Short leg 190 and long leg 192 may merge at approximately an angle 194 ranging from about 85 to 90 degrees. The short leg 190 includes a straight section for receiving the spring 184. The long leg 192 may be straight as shown, or more curved. As compared to the neck 104 and corresponding plug 102 of the previous embodiment (FIG. 6), the neck 104 and plug 102 may have a rectangular or other angular shape that fits between the tragus 20 and anti-tragus 22 to cover the ear canal 26. However, it is contemplated that the neck 104 of this particular embodiment may be round, oval, or any shape that functions to adequately cover the ear canal 26.

Torsion spring 184 may be permanently attached to the elbow 180 and sleeve 182 with an adhesive such as cyanoacrylate glue, casein glue, cement glues, resin glues. In the alternative, such connections may be made with an interference fit between the members.

Referring still to FIG. 10, in another embodiment of the present invention, the hearing protector 100 may differ from the previous embodiment by attaching the spring 184 to elbow 180 with a rotating connection. While the rotating connection may allow the elbow 180 to freely rotate with respect to spring 184, it is desirable that an increased resistance to rotation is experienced when the plug 102 is placed in or against the ear canal. This is to maintain adequate pressure against between the plug 102 and ear canal 26 opening, and thus, prevent plug 102 from falling away from the ear canal during use. The increased resistance may be achieved by a detent located between the spring 184 and the elbow 180. In the alternative, the increased resistance may be achieved other ways, such as by a screw thread. Regardless of the exact structure used to create increased resistance, it will likely be caused by material interference between the spring 184 and elbow 180. It is further contemplated that the spring 184 in this particular embodiment may be stiff enough to be ineffective as an actual spring.

Referring still to FIG. 10, in yet another embodiment of the present invention, the hearing protector 100 may be constructed from a flexible, semi-rigid unitary member (similar to the embodiment of FIG. 6) that is reinforced and/or aesthetically enhanced with additional components. In this embodiment, the shoulder region 106 is partly defined by an elbow 180. The elbow may merely be a cover constructed from a plastic or rubber type material, and may be the same in appearance or feel, or may be different. Likewise, sleeve 182 used to cover the arm 108, and may extend to partially cover the shoulder 106 as shown. The sleeve may be a cover constructed from a plastic or rubber type material, which may be the same in appearance or feel, or may be different. The section of shoulder 106 located between elbow 180 and sleeve 182 may be relatively straight for aesthetic reasons.

Figure 11:
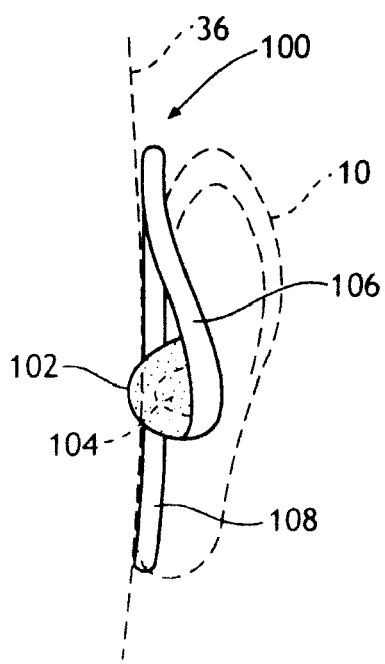
FIG. 11 is a front elevation view of a fifth embodiment of the hearing protector of the present invention, shown in a biased state as it engages an ear.
Figure 12:
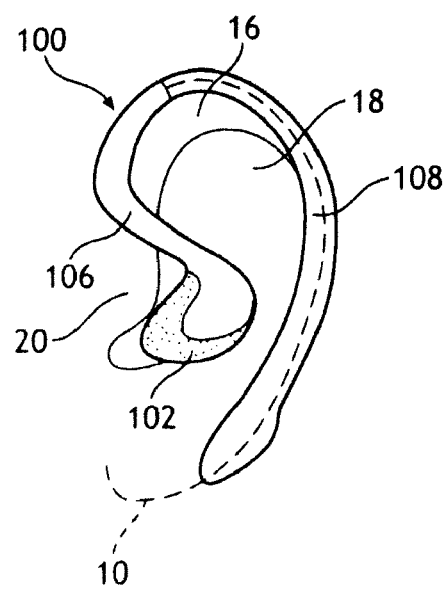
FIG. 12 is a side elevation view of the hearing protector of FIG. 11.

In another exemplary embodiment of the present invention, shown in FIGS. 11 and 12, hearing protector 100 may be of unitary construction, or may be constructed from three separate components. Desirably, the three components include a plug 102/neck 104; a shoulder 106; and an arm 108. In this embodiment, the plug 102 may like that described for the previous embodiments. The neck 104 may be integrally connected to the shoulder 106, which are formed from a rigid plastic such as polyethylene, polypropylene, polyvinyl chloride, and polycarbonate. Desirably, the arm 108 is attached to an end of the shoulder 106 opposite the neck 104.

Arm 108 may be the flexible plastic material as described for the embodiment of FIG. 6. Desirably, arm 108 is a relatively soft, pliable rubber-like material that is reinforced with an embedded stiffening wire. Arm 108 is joined to the end of shoulder 106 by an adhesive such as cyanoacrylate glue, casein glue, cement glues, resin glues. The stiffening wire is partially embedded into shoulder 106 for additional strength at this joint.

Additional embodiments of the hearing protector 100 of the present invention are depicted in FIGS. 13-25. These embodiments differ from the previous embodiments in that they may replace the ear plug 102 with a specially shaped pad that generally covers the ear canal 26 and a portion of the surrounding concha 24. This pad is referred to as an EAM pad 200. (The term "EAM" is an acronym for "external auditory meatus.") Further, force may be solely or partially applied to the EAM pad 200 by a pressure pad 202, as described below. This force will create pressure between the EAM pad 200 and the concha 24. It is contemplated that additional pressure, beyond that provided by the pressure pad 202, may be obtained by using the previously described biased bow member in conjunction with the pressure pad 202. However, the bow member is optional, as well as the handle 110. In some embodiments, a target indicia located on an exposed pressure plate 1208 may aid in positioning the EAM pad 200 and pressure pad 202. Further, a touch indicia located on the optional handle and/or bow will indicate to the wearer where to touch to position the hearing protector 100.

Figure 15:
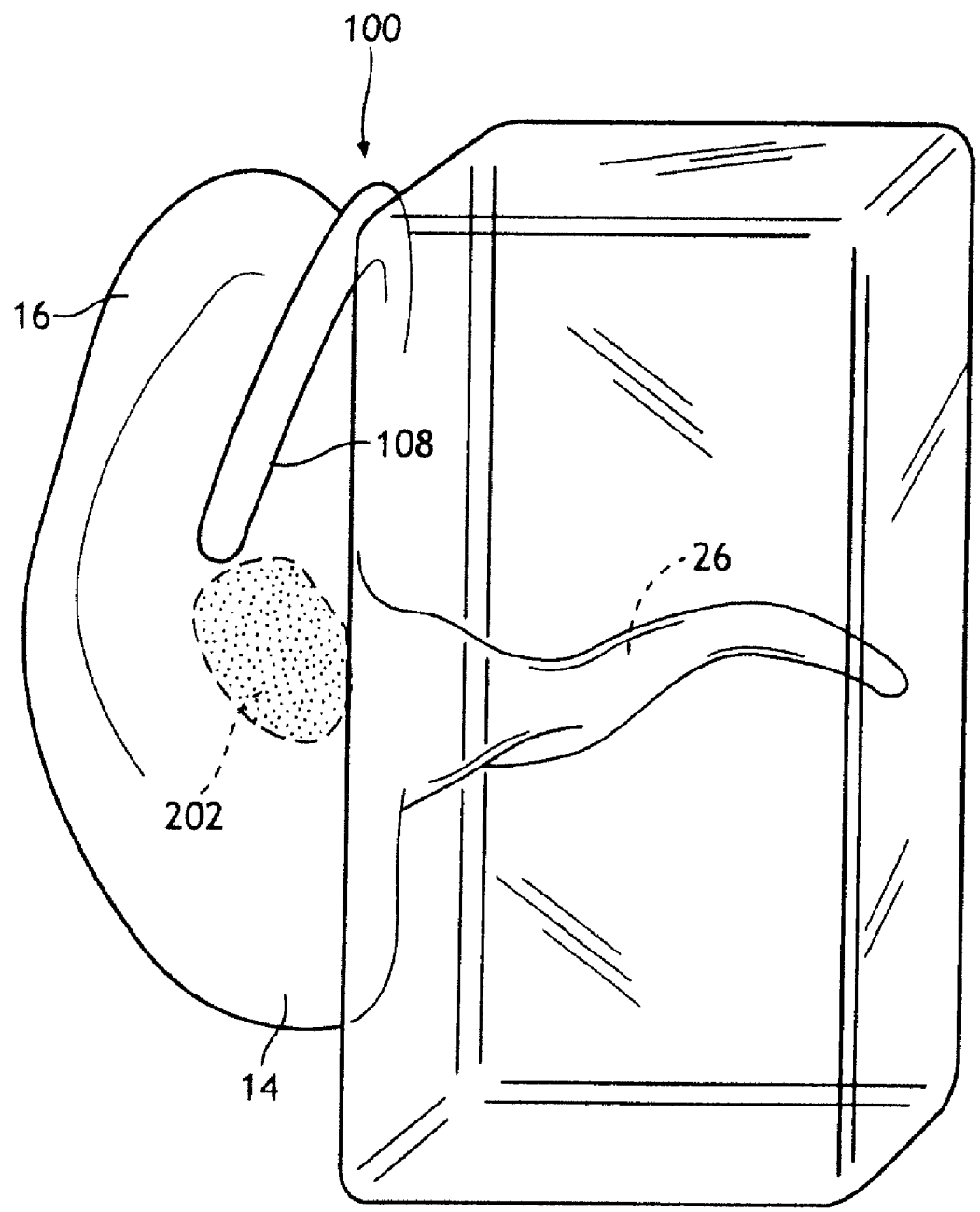
FIG. 15 is a rear perspective view of the hearing protector of FIG. 14.
Figure 16:
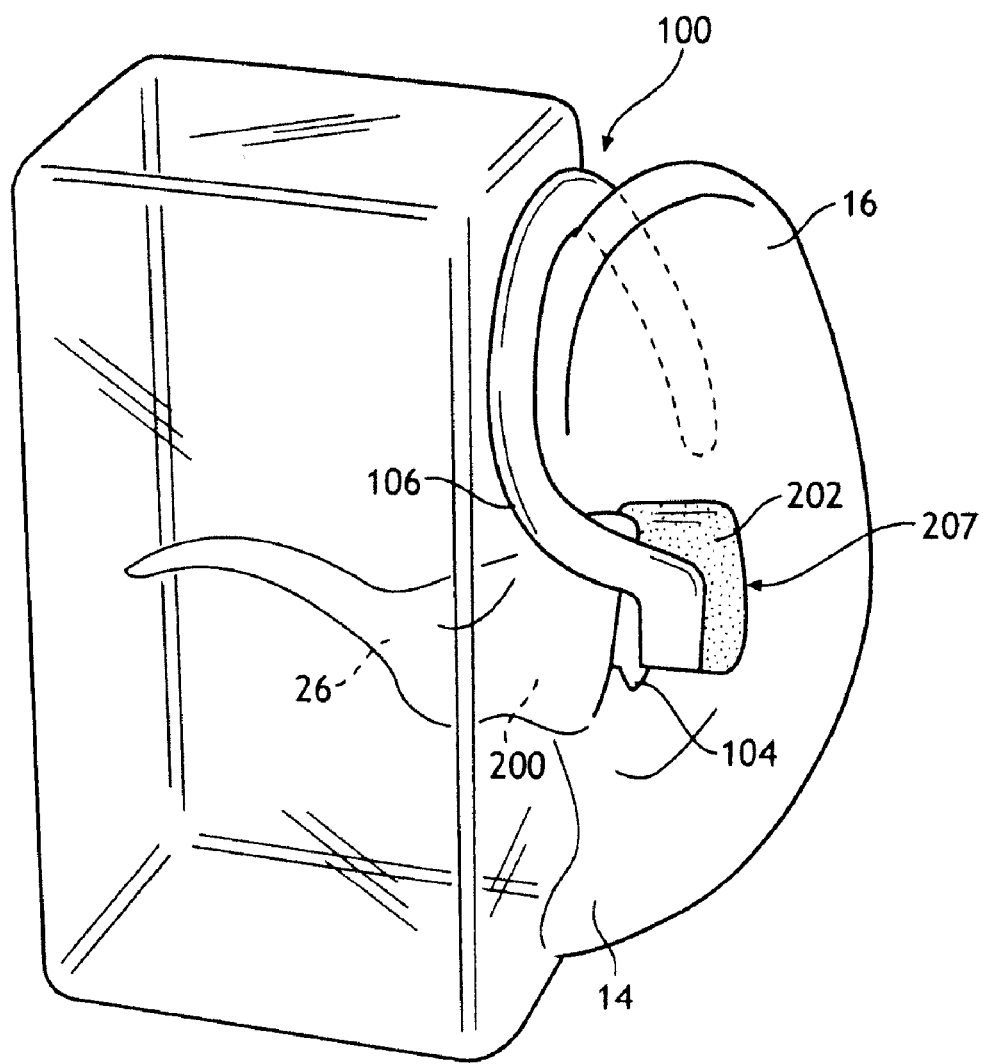
FIG. 16 is a front perspective view of the hearing protector of FIG. 14.
Figure 17:
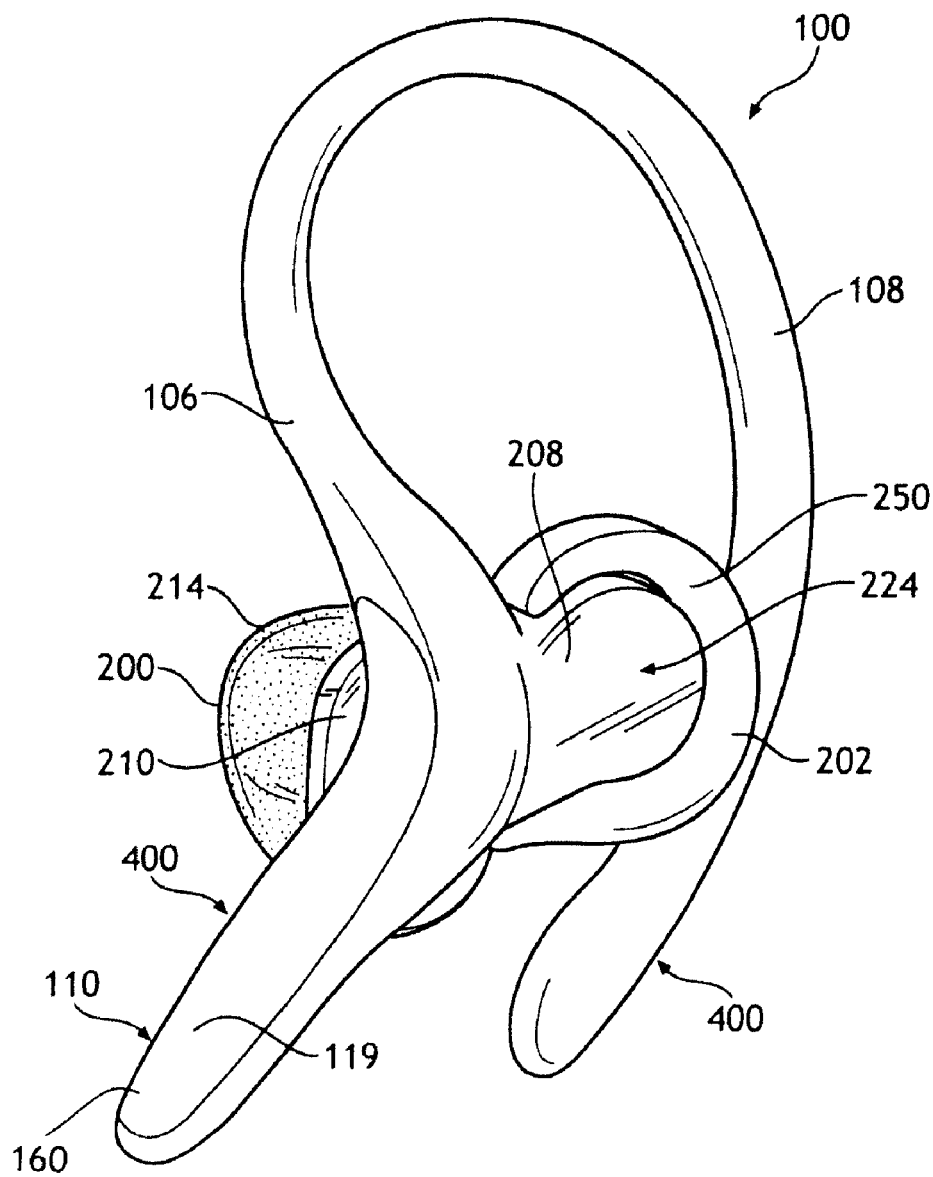
FIG. 17 is a side perspective view of a seventh embodiment of the hearing protector of the present invention, showing a pressure pad.

Referring now to the embodiments of FIGS. 13-16, the hearing protector 100 may be completely unitary in construction, or may be assembled from two or more separate parts. For instance, FIG. 13A depicts a separate EAM pad 200 connected to a neck 104. EAM pad 200 is a pliable member that may conform to a portion of the ear canal 26. The pressure pad 202 is connected to the shoulder 106 (FIG. 13A) or to an opposite surface of the neck 104 (FIGS. 14-16). The pressure pad 202 cooperates with the concha 24 to apply force to the EAM pad 200 so that it maintains a desired position with respect to ear canal 26, and may desirably, effect a seal between the pad 200 and concha 24 and/or ear canal 26.

The neck 104 may extend from a side of shoulder 106 or another surface thereof, such as the bottom edge 107 referenced in FIG. 13B. The neck 104, regardless as to its orientation with respect to shoulder 106, acts as a hub for EAM pad 200, and possibly, for pressure pad 202. Pressure pad 202 may instead be directly attached to the shoulder 106 and not directly attached to neck 104 (see FIGS. 13A and 13B).

Together, the shoulder 106 and arm 108 form the bow member that generally extends from the tragus 20, upward to where helix 16 meets tissue 36, and down around the pinna 12 adjacent to where concha 24 meets tissue 36. The arm 108 may or may not continue to wrap around and contact the lobe 14.

The EAM pad 200 and pressure pad 202 may be made from materials having the same or different physical and/or strength characteristics. In particular, the pads 200 and 202 may have the same or different elastic properties, density, compression strength, etc. Pads 200 and 202 may even have a unitary structure (not shown). Desirably, the EAM pad 200 is easier to compress and thus more conformable to the ear than the pressure pad 202. This strength property difference may be measured using a standardized test method to determine foam compression, e.g. Standard Test Methods for Flexible Cellular Materials—Slab, Bonded, and Molded Urethane Foams, ASTM-D-3574, American Society for Testing and Materials International, 2005, incorporated herein by reference to the extent it does not conflict with the present invention.

Appropriate materials from which the pads 200 and 202 may be made include all the foams previously listed for plug 102. In addition, the pads 200 and 202 may be constructed from other compliant elastic materials such as silicone, rubber, and the like, regardless of whether or not they have a foam cell-structure. In one embodiment, pad 200 is a foam material as described above, and pad 202 is constructed from a silicone material. Rubber and silicone materials may be characterized by hardness measurements such as those that may be obtained by using the following test method incorporated herein to the extent it is consistent with the present invention: Standard Test for Rubber Property-Durometer Hardness, ASTM 2240-05, American Society of Testing and Materials International, 2005. Desirably, the pressure pad 202 may be of greater hardness than the EAM pad 200.

In another and possibly more cost effective embodiment, pads 200 and 202 are made from the same material, and may even be integrally connected. The term "integral" is used herein to mean that two or more parts have a homogenous or continuous connection therebetween. The term "unitary" is used herein to mean a direct, permanent connection that connects more than one part, such as by adhesion, fusing, welding, or the like. For example, the neck 104 could extend from the bottom surface of shoulder 106, and unitary pad 200/202 could extend outwardly from each side of neck 104 and shoulder 106. In one example, the pads 200/202 could be similar to the separate pads 200 and 202 shown in FIG. 13B, except that the volume between the separate pads could be bridged with a material, either the same as or different to either or both pads 200 and 202. This bridging material may have an integral or non-integral connection between the pads 200 and 202. Non-integral connections include permanent welded, fused, or adhesive connections, and the like.

Figure 19:
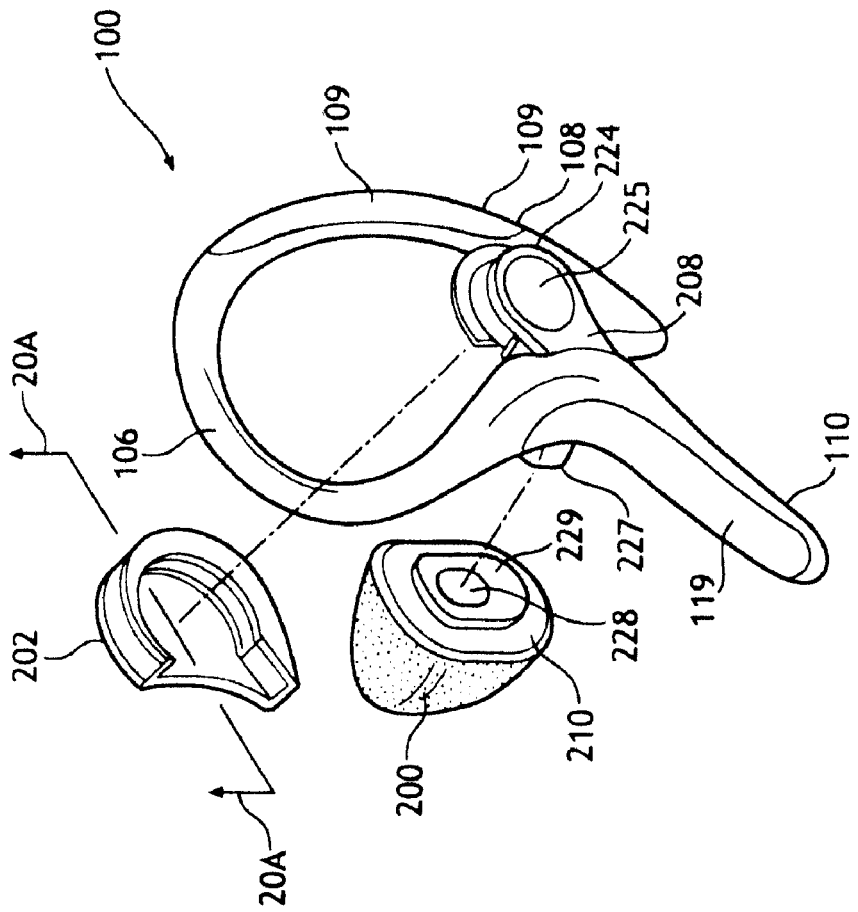
FIG. 19 is an exploded view of the hearing protector shown in FIG. 17.
Figure 18:
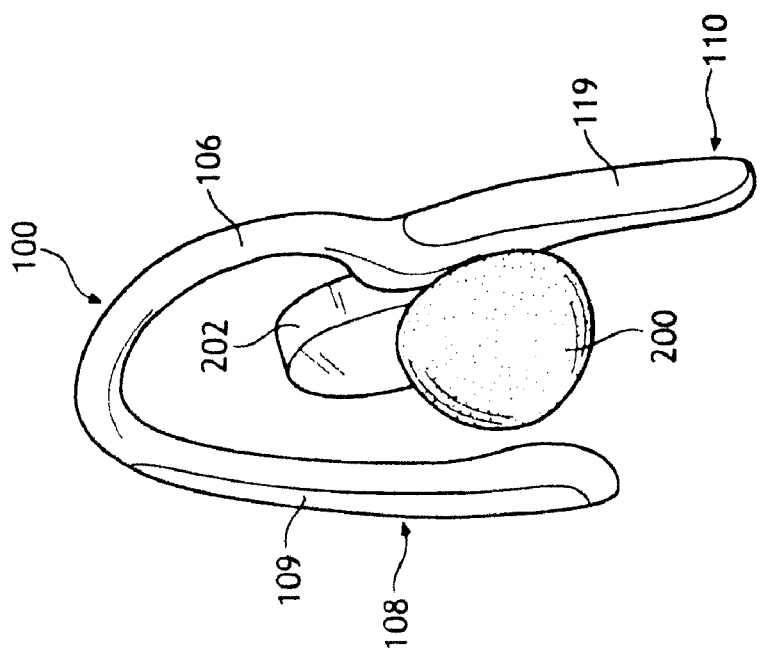
FIG. 18 is an opposite side perspective view of the hearing protector of FIG. 17.

Most desirably, the EAM pad 200 is shaped so that it may be substantially or fully disposed against a human ear canal. While human anatomy may vary between persons, the conformity of the material from which the pad is made will be able to compensate for most variances, and thus will be comfortable for most persons. However, it is contemplated that the EAM pad 200 could be made available in different sizes to achieve a more custom-like fit. The shape of the EAM pad 200 may somewhat resemble an elliptical dome with a nearly elliptical-shaped footprint visible at flat side surface 210 (FIG. 19). The EAM pad can be configured to partially or fully engage or be disposed against the ear canal, such as with ear caps or semi- and full-insert plugs.

So that the EAM pad 200 effects a seal against the ear canal, there are no creases, cavities or pockets on the domal surface 214. Desirably, the material from which the EAM pad is constructed has a skin on its outer surface to so that it may be easier to clean the surface for repeated use. The seal against the ear may not be perfect due to skin texture or an irregularly shaped ear canal. However, the seal is effective enough to prevent significant sound energy from entering the ear canal.

Pressure pad 202, unlike the EAM pad 200, does not need to create a seal for noise control, but some sound attenuation may occur by its presence. The primary function of pressure pad 202 is to apply force to the EAM pad 200 to remain partially or fully engaged with or disposed against the ear canal 26. In use, the pressure pad 202 is compressed between the concha 24 and the neck 104, see FIGS. 15 and 16. Because the concha 24 is not aligned with the ear canal 26 as viewed from a side (FIG. 16), the pressure pad 202 may be offset from the EAM pad 200 (FIGS. 13A and 13B).

Desirably, the pressure pad 202 is attached to a pressure plate 208 that extends from shoulder 106 adjacent the neck 104. Pressure plate 208 may be a blade-like structure that extends from the shoulder or neck (see FIG. 20). Desirably, pressure plate 208 is part of the unitary ear clip structure, and is rigid enough so that it does not bend significantly when pressed in order to adjust the fit of the EAM pad 200 and/or pressure pad 202. In another embodiment, the pressure plate 208 may be selectively removable as described herein.

The pressure pad 202 may be shaped for comfort, and if desired, for aesthetics. For reasons of comfort, the edges 252 (see FIG. 13B) may be rounded to mitigate or create fewer pressure points on the pinna and concha areas of the ear respectively. For reasons of aesthetics, it is contemplated that there may be a pattern or indicia printed or exhibited as a relief on the outer surface 207 of pressure pad 202. Desirably, in this particular embodiment of the present invention, the shape of the pressure pad 202 may be a roughly oval or circular discoid, and may be made as small as possible to reduce material costs, while at the same time serving to create the desired pressure between the neck 104 and concha 24.

EAM pad 200 may connect to neck 104 in a variety of ways, such as the methods depicted in FIGS. 8A-8D. Further, the EAM pad 200 be connected to neck 104 by a ball and socket, hook and loop, magnets, adhesive, or any other connection that may be selectively undone by the user. For instance, the neck may be connected to a stem with a ball-shaped receiver or other connections as described below with respect to FIG. 19.

The thickness of the pad 200 may be lesser or greater than is shown, and is dependent on the stiffness of the material used for the pad. Desirably, the EAM pad 200 is thick enough so that the wearer cannot detect any rigid plastic portions such as the neck 104 or anything protruding therefrom.

Shoulder 106 is a section of the hearing protector 100 that will likely experience various stresses as it is bent for placement about the pinna. While in this particular embodiment shoulder 106 is not stressed significantly after it is in place about the pinna, it is contemplated that in other embodiments, shoulder 106 may operate in part as the spring member of hearing protector 100. Shoulder 106 may have a curved appearance when viewed from the side, similar to the embodiment shown in FIG. 12. However, it is contemplated various other curvatures or aesthetic shapes may be incorporated into the shoulder 106 shape without affecting functionality.

In FIGS. 17-20, yet another embodiment of the hearing protector 100 is depicted. This embodiment generally differs from that shown in FIG. 13 in several ways. First, it includes an optional handle 110. As described above, handle 110 may include a material overlay 119 for functional or aesthetic purposes. Second, hearing protector 100 may include an exposed pressure plate 208 onto which the corresponding pressure pad 202 is attached. Third, the arm 108 may include an optional material overlay 119 for functional or aesthetic purposes. The bow member is similar to that shown in the embodiment of FIG. 6, except that the bow member may not act as a torsion spring. The EAM pad 200 may be identical to that shown in the embodiment of FIG. 13.

Optional touch indicia 400 may be located on the optional handle 110 and/or bow member 108 and serve to indicate where the user should touch the hearing protector 100 for the positioning thereof. The touch indicia may be defined by a different material, color, texture, and/or symbols. For example, the overlays 109 and 119 define a touch indicia 400 for the embodiment shown in FIG. 20. Touch indicia may look and/or feel different to the user.

Referring to FIG. 20, the pressure plate 208 extends from neck 104, and is oriented perpendicularly with respect to the stem 120 in both the z-direction 230 and y-direction 232. In one embodiment, there is an integral connection between neck 104 and pressure plate 208. The portion of shoulder 106 in the immediate vicinity of the pressure plate 208 is generally oriented in z-direction 230. In another embodiment (not shown) pressure plate 208 may be detached and replaced from the ear clip structure. For example, a replacement unit defined by a pressure pad 202 and corresponding pressure plate 208 may be selectively detached and replaced from the neck 104 or shoulder 106. It is contemplated that the connection may include a ball and socket, hook and loop, magnets, adhesive, or any other connection that may be selectively operated by the user.

Pressure plate 208 may have a rounded shape such as a hemi-discoid shaped body, shown. On the outer plate surface 221 of the pressure plate 208 (which will face the ear when in use), there may extend a flange 222. Flange 222 may be an arcuate shape or any shape that corresponds to the shape of pressure pad 202.

Referring to FIG. 19, the pressure-plate face 224 (opposite to surface 221) may have a surface indicia such as an exposed flat surface or a patterned surface. For instance, as seen in FIG. 19, the face 224 includes a surface indicia in the form of a detent 225 to indicate to a user that this is an area to which pressure may be applied with a finger to adjust the EAM pad or the pressure pad. While a circular detent 225 is depicted in this exemplary embodiment, any texture, pattern or indicia may be used for this purpose, such as a raised pattern or color indicator.

Stem 120 may have a ball-shaped receiver 227 that corresponds to a socket feature 228 on the EAM pad 200. Preferably the socket feature 228 is defined by a cavity in a separate frame member 229 that engages the stem 120 and ball-shaped receiver 227. The EAM pad 200 is affixed to the frame member 229 in the ways described previously with respect to FIGS. 8A-D. The separate frame member 229 may be made of materials similar to the hearing protection device 100, but may also be made of a soft flexible material. However, any other connection between neck 104 and EAM pad 200 may be used (e.g. hook and loop, magnets, adhesives, and the like).

The pressure pad 202 of FIGS. 17-20A is different from the embodiment of FIG. 13 in that desirably, it wraps only partially about a pressure plate 208 in order to leave a portion of the pressure plate exposed. The pressure pad 202 has the same general shape as the pressure plate 208 when viewed from the x-direction 226. As seen best in FIG. 20A, a lip 250 extends from the outer face 207 of the pressure pad 202, the lip 250 being configured to wrap about the flange 222 on pressure plate 208. The inner face 254 of pressure pad 202 may make direct contact with the pressure plate outer surface 221, or may include an adhesive material therebetween.

For any of the embodiments shown in FIGS. 13A-25, the EAM pad 200 and the pressure pad 202 may be made of the same material (e.g. viscoelastic foam) and characterized by one or more material properties. For example, the density of the EAM pad 200 and the pressure pad 202 may be about 2[32.0 Kg/m3] to about 20 lbm/ft3 [320.4 Kg/m3]. More desirably, the density of the EAM pad 200 and the pressure pad may be about 3[160.2 Kg/m3] to about 10 lbm/ft3 [240.3 Kg/m3] (see ASTM 3574-05, previously incorporated). The compression force deflection at 25 percent (see, ASTM 3574-05, previously incorporated) is desirably between about 0.3 psi [0.02 Kg/cm2] to about 10.0 psi [0.73 Kg/cm2], and more desirably between about 0.3 psi [0.02 Kg/cm2] and about 4.0 psi [0.29 Kg/cm2]. The foam can further be described by cell size which may be determined using the following test method incorporated herein to the extent it is consistent with the present invention: Standard Test Method for Open-Celled Content of Rigid Cellular Plastics by the Air Pycnometer, ASTM 2856-94, American Society of Testing and Materials, Annual Book of ASTM Standards, 1998. Desirably, the cell size is a minimum of about 80 pores per inch, and more desirably a minimum of about 100 pores per inch. The cell structure may be further defined as having between about 30 percent to about 70 percent open cells, and more desirably between about 40 percent to about 60 percent open cells. In addition, the recovery time for the foam material may be desirably between about 2 seconds to about 120 seconds, but more desirably between about 8 seconds to about 20 seconds. See, ASTM D 3574-05, infra. Furthermore, the water absorption of the foam may desirably be less than about 20 percent, and more desirably, less than about 5 percent as measured by test method incorporated herein to the extent it is consistent with the present invention: Standard Test for Water Absorption 25 Hour/Equilibrium, ASTM D570, American Society of Testing and Materials.

For any of the embodiments shown in FIGS. 13A-25, the pressure pad 202 may be made of different materials than the foam used to construct EAM pad 200. For example, the pressure pad 202 may be described as an open cell or reticulated foam material which may be characterized by several material properties as determined by the test methods noted above. When reticulated foam is used as the pressure pad 202, the density of the foam may be about 1.2 to about 2.6 lbm/ft3 [19.2 to 41.6 Kg/m3]. More desirably, the density of both the EAM pad 200 and the pressure pad 202 may be about 1.5 to about 1.9 lbm/ft3 [24.0 to 30.4 Kg/m3]. The compression force deflection at 25 percent is desirably between about 0.4 to about 2.0 psi [0.03 to 0.14 Kg/cm2], and more desirably between about 0.65 to about 1.2 psi [0.04 to 0.08 Kg/cm2]. The foam may further be described by the cell size, and desirably has a cell size between about 40 to about 80 pores per inch, and more desirably between about 50 and about 70 pores per inch. The cell structure may desirably have between about 40 to about 80 percent open cells, and more desirably between about 50 to about 70 percent open cells. The recovery time for the foam material may be desirably between about 1 second to about 20 seconds, and more desirably be between about 2 seconds to about 4 seconds. The water absorption of the foam may be desirably less than about 20 percent, and more desirably less than about 5 percent.

Desirably, the thickness of the pad as measured between the outer face 207 and inner face 254 may be about 0.5 to about 6.0 mm. More desirably, the thickness of the pad as measured between the outer face 207 and inner face 254 may be about 1.0 to about 3.0 mm.

In FIG. 21, a further embodiment of the hearing protector 100 is depicted. This embodiment is almost identical to the embodiment described with respect to FIGS. 17-20 except the bow member is omitted. Specifically, there is no shoulder 106 or arm 108. Whilst the bow member may provide a measure of security against loss of the hearing protector 100 during wear, the advantage provided by omitting the bow member is that there is nothing over the user's ear (near junction 170, FIG. 2) that would interfere with the wearing of eye glasses. Handle 110 provides a grip for positioning and removing hearing protector 100 from the ear. All other previously described variations including but not limited to the use of unitary pads 200/202 or handle overlay 119 shall apply to this embodiment.

Figure 22:
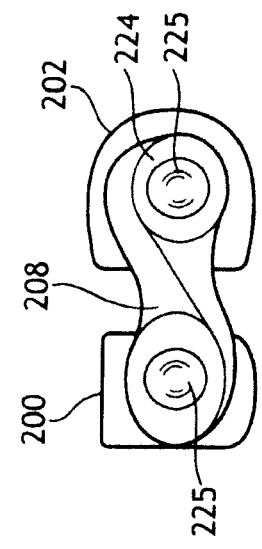
FIG. 22 is a side elevation view of the ninth embodiment of a hearing protector of the present invention.
Figure 23:
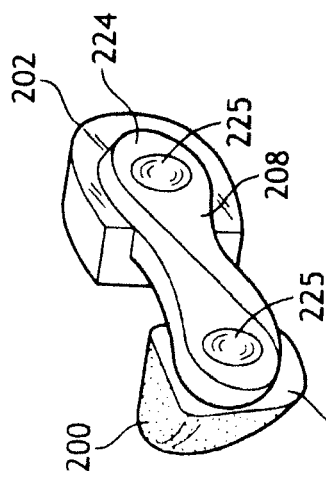
FIG. 23 is a front perspective view of the hearing protector of FIG. 22.

In FIGS. 22-23, still another embodiment of the hearing protector 100 is depicted. This embodiment is almost identical to the embodiment described with respect to FIG. 21 except the handle 110 is omitted. The advantage of this hearing protector is that it may be more comfortable for some than other hearing protectors that significantly enter the ear canal 26 (e.g. a foam ear plug that is compressed prior to insertion into the ear canal, and allowed to expand so that it stays in place). All other previously described variations including but not limited to the use of unitary pads 200/202 shall apply to this embodiment.

Yet another embodiment is also contemplated wherein the handle 110 is omitted and the bow member is connected the hearing protector of FIG. 21 and FIG. 22. This configuration allows the hearing protection device to wrap around the pinna to provide increased security to the user. Furthermore, this allows increased adjustment to users whose facial width limits the insertion depth of the EAM pad.

Figure 25:
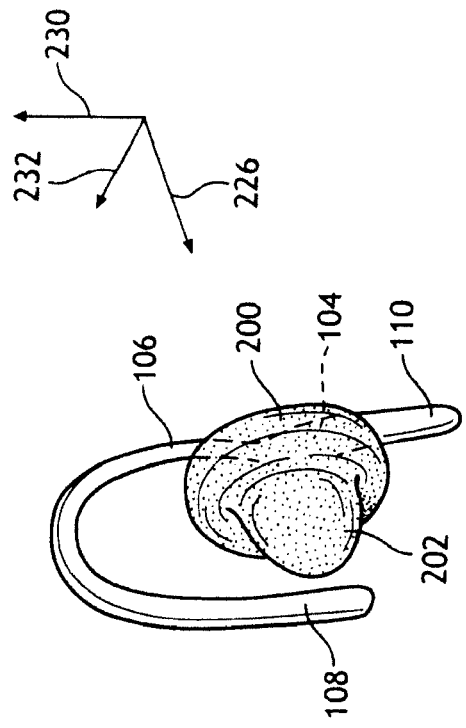
FIG. 25 is a front perspective view of the hearing protector of FIG. 24.
Figure 24:
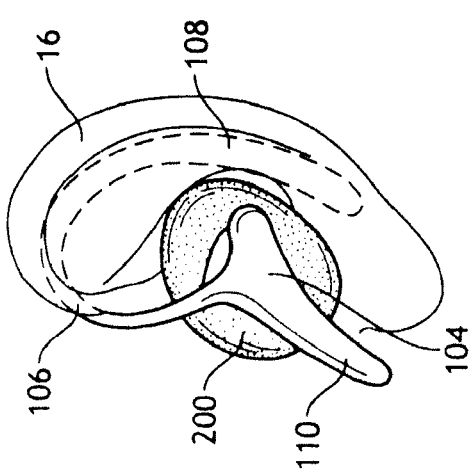
FIG. 24 is a side perspective view of the tenth embodiment of a hearing protector of the present invention.

Finally, in FIGS. 24-25, another embodiment of the hearing protector 100 is depicted. This embodiment is similar to the embodiment described with respect to FIGS. 22-23 except the pressure plate is enlarged and it may include additional sound attenuation for the EAM pad 200 and the pressure pad 202, such as has been described previously. In addition, the pressure pad 202 and EAM pad 200 are unitary in construction, and possibly integrally connected. In this particular embodiment, the pressure pad 202 attaches to the neck 104, and the EAM pad 202 is attached to the pressure pad 202. By outward appearance, the pressure pad is sandwiched between the EAM pad 200 and the neck 104. However, internally, the neck 104 may have flange extending therefrom that would provide stiffening for pressure pad 202 (similar to flange 222 at FIG. 20), and/or the neck may include a stem or the like extending into the EAM pad 200 (similar to that shown in FIGS. 6-8). The entire EAM pad 200/pressure pad 202 assembly may be selectively attachable by ball and socket, hook-and-loop, and magnet connections, or the like, as described previously.

The configuration shown in FIGS. 24-25 provides the advantages of a muff-style hearing protector without a head band or other attachment about the pinna. Further, it may be easier to remove and replace than some muff-style designs. As shown in FIGS. 24 and 25, the pressure plate is enlarged enough to fill or almost fill the area defined by the concha 24 and the anti-helix 18. Because human anatomy is varied from individual to individual, the dimensions of the pressure plate 208 in the y-direction 232 and z-direction 230 may be such that it fits most adults. It is contemplated that a variety of sizes may be offered. With respect to FIGS. 17-20, it is contemplated that in yet another embodiment, the pressure plate 208 may be configured as shown and described for the hearing protector of FIG. 24.

Referring now to FIGS. 6-7, 9-12, and 17-20, it is further contemplated that the arm member 108 may be shortened or even removed for easier placement onto the ear. With respect to FIGS. 17-20, it is contemplated that the pressure plate 208 may be configured as is shown in FIGS. 24-25. It is further contemplated that the embodiments shown in FIGS. 13-20 may have the EAM pad 200 replaced by an ear plug design such as those shown in FIGS. 3-4.

The next set of embodiments as shown in FIGS. 26 through 49 show different varied combinations of the EAM pad 200 and pressure pad 202. While each of these embodiments are shown in conjunction with a complete ear clip, the shoulder 106, the arm 108, and/or handle 110 may be omitted as described previously. Generally, in each of embodiments of FIGS. 26 to 41, the EAM pad 200 and pressure pad 202 are connected, and desirably, are integrally connected. The separate frame member 229 onto which the EAM pad 200 and pressure pad 202 components are attached may be selectively removed from the ear clip neck 104. This allows the user to replace dirty or worn EAM pads 200, or to exchange one type of EAM pad with another style preferred by the user.

EAM pad 200 and pressure pad 202 may be collectively referred to as a replacement pad 300 when they are attached together as seen in FIGS. 26-49, even if each separate pad region is made from different types of material. Desirably, the replacement pad 300 is constructed by a molding process such as by injection molding, reaction injection molding, or the like.

The entire replacement pad 300 may be attached to the frame member 229 either temporarily or permanently; temporarily by an attraction, adhesion, or a friction/interference fit between the parts, and permanently by an adhesive or the like. Several non-limiting examples of temporary attachments include magnetics, hook and loop, slides, snaps, ball and socket, temporary adhesive, and the like. One non-limiting example of a permanent adhesive is a flexible rubber adhesive, such as Super Crystal Clear Waterproof Cement, available from Power Proxy located in Sussex, Wis.

The separate frame member 229 and replacement pad 300 are collectively referred to as a replacement assembly 310. It is contemplated that the replacement assembly 310 may be made from a single piece of material (either homogenous or composite), rather than a two-part construction, as shown. Furthermore, it is contemplated that at least the frame member 229 could be permanently affixed to an ear clip, and not actually be replaceable with respect to the ear clip.

Desirably, the replacement pad assembly 310 may be designed to have a symmetric configuration, thus allowing a single configuration of replacement assembly 310 to be used on either a right- or left-sided ear-clip. This single configuration will reduce the number of specialized parts and costs associated with the manufacture and sale of the replacement assembly 310. In addition, the need for only one configuration of replacement assembly 310 is more convenient for users.

The shape of each user's ear varies, and in particular, the size of the ear canal 26 varies among the population. Thus, preferred fit is one reason a particular design of EAM pad 200 may be selected by a user over another design. Some persons may find the EAM pad 200 more comfortable within a certain range of EAM pad diameters, shapes, materials, contours, and/or lengths.

As seen by way of example in FIG. 30, the EAM pad 200 has a width 304, and the pressure pad 202 has a width 306. Each width measurement is taken at the fullest part of the component when viewed in the x-y plane. As seen in FIG. 30, the replacement assembly 310 has a longitudinal axis 302 (as seen in the x-y plane) about which the pad 300 is symmetric.

Figure 49:
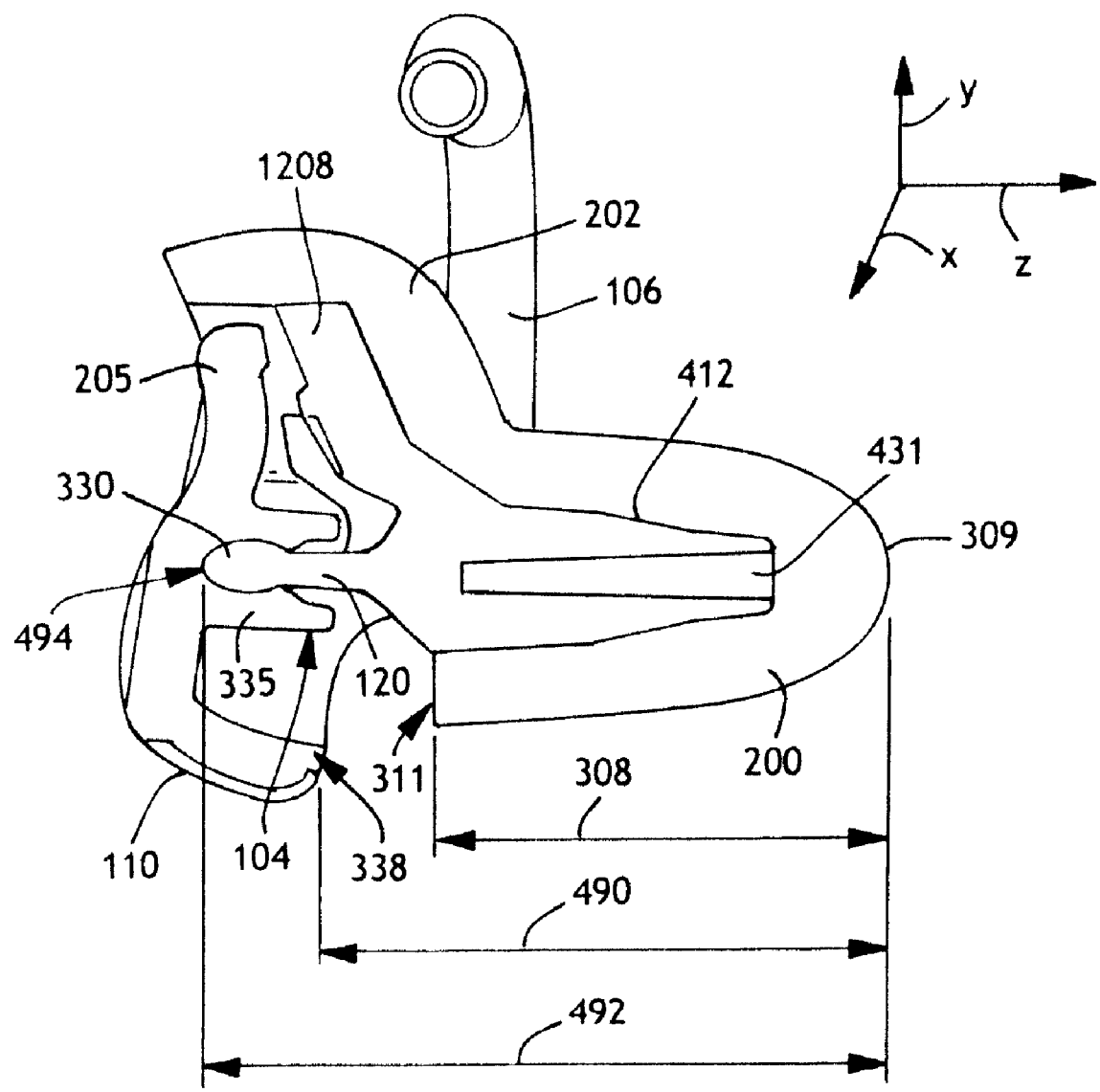
FIG. 49 is a cross section of the ear clip of FIG. 27.

Referring now to FIGS. 28 and 49, the EAM pad has a pad length 308, measured in the z-direction, from the highest portion of the distal end 309 to edge 311. Desirably, the EAM pad 200 itself has a length between about 6 to about 29 millimeters, and more desirably between about 15 to about 26 millimeters in length. The EAM pad has other lengths associated with it. An "active length" 490 is defined at the distance between pad distal end 309 and inside handle surface 338. The "overall length" of the replacement assembly 310 is the distance 492 between the pad distal end 309 and the distal end 494 of stem head 330. The active length range is from about 15 mm to about 30 mm, and desirably, about 18 mm to about 27 mm.

The active length of the replacement assembly 310 has a direct impact on the ability of the hearing protector 100 to attenuate sound. The depth that the EAM pad 200 is inserted into an ear canal 26 is directly related to the sound attenuation that can be achieved by that hearing protector 100. It is noted that the length of the stem 120 can influence the active length 490, and thus influence how far the EAM pad 200 can be inserted into an ear canal 26. However, this insertion depth is ultimately limited by the pressure pad 202, handle 110, or other components transverse to the ear canal 26. (The term "transverse" is defined as a direction cross-wise to the entrance of an ear canal, such that it prevents the EAM pad 200 (or plug 102) from entering into an ear canal, at least past a certain depth. This transverse direction need not be exactly parallel to a sagittal plane of the body, defined as a plane that divides the body into left and right portions. For example, as can be seen in FIG. 27, at least one of the handle 110 and/or the pressure pad 202 will interfere with the anti-tragus 22 or other parts of the ear and thus help the user to experience repeated comfort and effectiveness with each use. This interference allows the EAM pad 200 to be inserted into the ear canal 26 to a "predetermined depth range" which is directly dependent on the active length range. Desirably, the handle 110 serves only as a handle and not a connector to a lanyard, electrical cord, or the like to prevent the EAM pad from accidentally being pulled out of position.

Therefore at least one of the pressure pad 202, handle 110, and ear clip shoulder 106 may limit the insertion depth of the EAM pad 200 when contacting the body during insertion of the hearing protector 100, and prevent the EAM pad 200 from entering the ear canal past a predetermined depth range. This will provide repeatability of insertion depth and attenuation between uses. Attenuation may be measured according to the following test method incorporated herein: ANSI S3.19-1974 (R 1979) (ASA 1-1975), American National Standard, "Method for the Measurement of Real-Ear Protection of Hearing Protectors and Physical Attenuation of Ear Muffs," published by the Acoustical Society of America.

Desirably, the active lengths described herein can be independently achieved from a wearer's left side to right side. Specifically, the right-side hearing protector is independent of the left side so that a wearer can remove one hearing protector without affecting the other. This effect cannot be achieved by a head-band style ear plugs or ear-muff style hearing protectors which are connected to each other.

Shown in FIGS. 26-31 is just one embodiment of an ear clip having a first configuration of a replacement assembly 310. The view of FIG. 28 is a cross-sectional view of the replacement assembly 310 taken at the longitudinal axis of the x-y plane. Overall, the EAM pad 200 has a domal shape. The domal shape can generally be described as a cylinder with a rounded distal end 309. This EAM pad 200 may have the EAM pad diameter, material, contour and length described herein.

Referring now to FIGS. 28 and 31, adjacent and integral to the EAM pad 200 is the pressure pad 202. As demonstrated by the support frame member 229 located underneath the replacement pad 300, there may be an obtuse angle 402 formed between the exposed surface 408 of the pressure plate 1208 and a vertical axis 410 of the EAM pad support 412. This obtuse angle 402 may allow the EAM pad 200 to align and extend into the ear canal 26 as far as possible.

Figure 37:
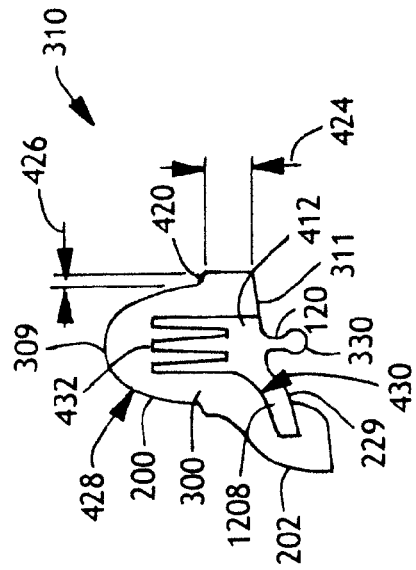
FIG. 37 is a cross-sectional view of the replacement assembly shown in FIG. 36.

Referring now to FIGS. 36-39, shown is a hearing protector 100 with a second embodiment of replacement assembly 310. The view of FIG. 37 is a cross-sectional view of the replacement assembly 310 taken at the longitudinal axis 302 of the x-y plane. The EAM pad 200 on this particular replacement assembly 310 has a stepped domal shape. The stepped domal shape is similar to the domal shape except that it has an added flange 420 surrounding the edge 311 of the EAM pad 200. This flange 420 may be either more or less prominent in both height 424 and thickness 426. For example, the flange 420 shown in FIG. 40 has both a height 424 and thickness 426 that is greater in dimension than that shown in FIG. 36. The purpose of flange 420 is seal the opening of the ear canal 26 to block sound from entering the ear canal.

Figure 39:
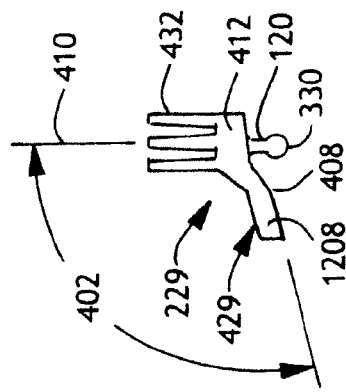
FIG. 39 is a side elevation of the support frame member shown in FIG. 37.
Figure 36:
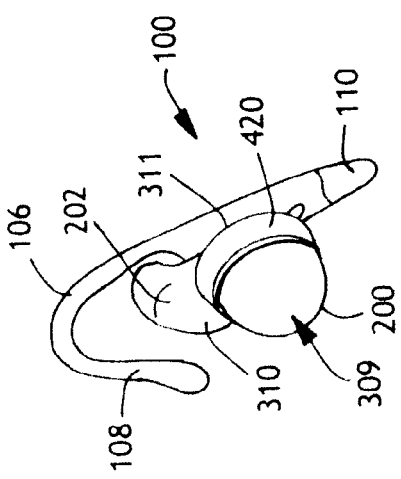
FIG. 36 is perspective view of a thirteenth embodiment of a left-side version of a hearing protector of the present invention.
Figure 38:
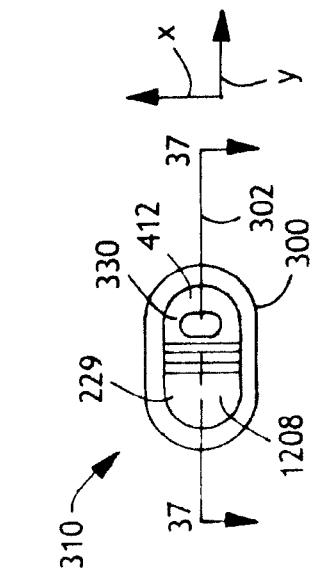
FIG. 38 is a bottom plan view of the replacement assembly shown in FIG. 37.
Figure 40:
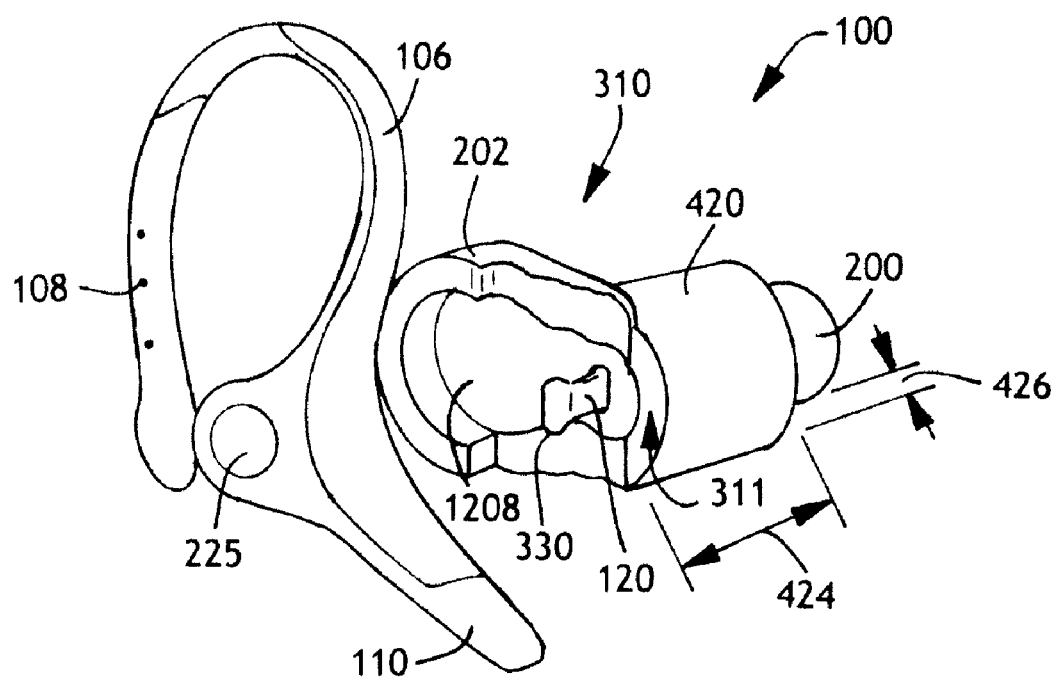
FIG. 40 is a partially exploded view of an alternative embodiment of the hearing protector.

As with the previous embodiment, there exists an obtuse angle 402 between the vertical axis 410 and the exposed surface 408 of the pressure plate 1208 (see FIG. 39). However, it is noted that when the flange 420 is prominent enough (e.g. thick enough), it is also a structure transverse to the ear canal 26 that could be used to regulate insertion depth of the pressure pad 200 within the ear canal 26.

Figure 33:
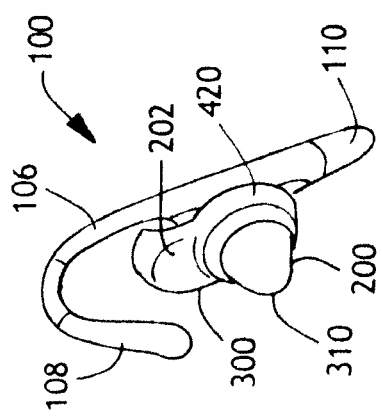
FIG. 33 is a cross-sectional side view of the replacement assembly shown in FIG. 32.
Figure 34:
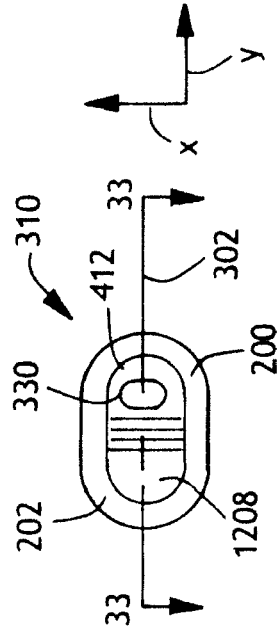
FIG. 34 is a bottom plan view of the replacement assembly shown in FIG. 33.

Referring now to FIGS. 32-35, shown is a hearing protector 100 having a third embodiment of a replacement assembly 310. The view of FIG. 33 is a cross-sectional view of the replacement assembly 310 taken at the longitudinal axis 302 of the x-y plane. The EAM pad 200 of this replacement assembly 310 has a stepped cone shape. The stepped cone shape is similar to the stepped dome shape, except that the flange 420 may have a decreasing radius as it extends in the z-direction, and the rounded dome shape may be replaced by a pointed dome or cone shape.

Figure 35:
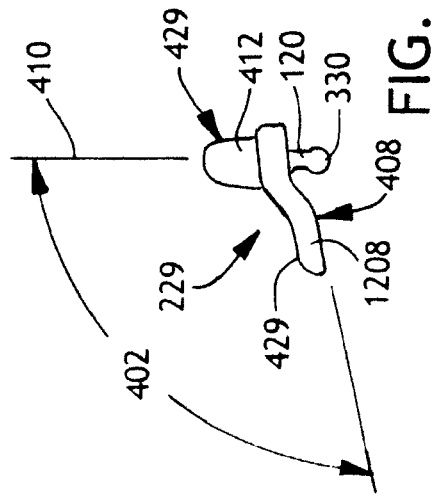
FIG. 35 is a side elevation of the support frame member shown in FIG. 33.

As with the previous embodiment, there exists an obtuse angle 402 between the vertical axis 410 and the exposed surface 408 of the pressure plate 1208 (see FIG. 35). Again, it is noted that when the flange 420 is prominent enough (e.g. thick enough), it is also a structure transverse to the ear canal 26 that could be used to regulate the insertion depth of the pressure pad 200 within the ear canal 26.

It may be that each replacement pad 300 has a wall thickness (defined as the thickness between an exterior surface 428 and an interior surface 430) that is somewhat constant so that uniform support is applied to the replacement pad 300 by the support frame member 229 during insertion of the EAM pad 200 into the ear canal 26. In the alternative, it may be more desirable that more padding could be added in certain places, such as at distal end 309, and less padding at the pressure plate 1208 so that the pressure plate can apply more direct pressure to the ear. Referring to FIGS. 28 and 33, the interior surface 430 of the replacement pad 300 may have a similar contour as the exterior surface 428.

Referring now to FIGS. 28, 31, 33 and 35, each of the EAM pads 200 may be supported by various styles of support frame members 229. While it may be possible to use a generic configuration of support frame member 229 to support a replacement pad 300, it may be desirable to have a support frame member 229 that is contoured so that it has a shape similar to the replacement pad 300. For example, an exterior surface 429 of the support frame member may appear to be a smaller version of the replacement pad 300. Desirably, the exterior surface 429 of the support frame makes substantial contact with the interior surface 430 of replacement pad 300.

The replacement pad 300 may be made of the same materials as described in previously described embodiments for plug 102. Further, the replacement pads 300 may be made from a flexible thermal plastic rubber (TPR) material or silicone so that it can be washed with a cleaning substance for repeated use. However, the replacement pads may be made from any flexible thermoplastic materials such as thermal plastic elastomer (TPE) and thermal plastic urethane (TPU).

The support frame 229 may be constructed from the same materials as previously described. Because the support frame 229 may be an injection-molded part, it too may have a somewhat even thickness throughout the entire part for even cooling to ensure dimensional stability of the molded part. Thus, in each of the support frames shown in FIGS. 28 and 33, the support frame member 229 supporting EAM pad 200 has a cavity 431 for the purpose of removing material from the relatively thick portion supporting the EAM pad 200.

Figure 41:
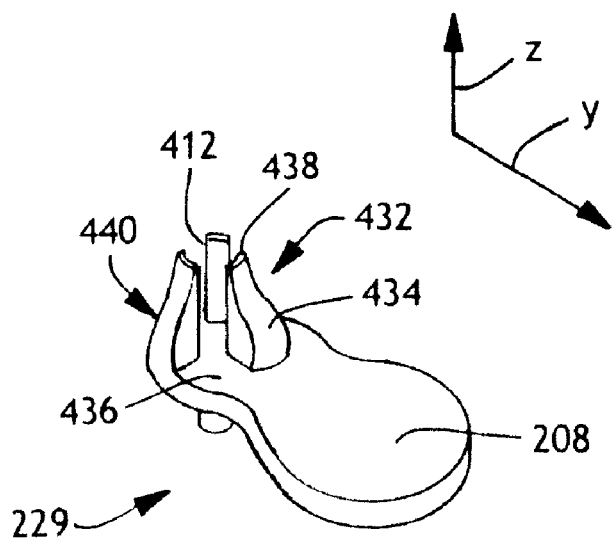
FIG. 41 is a perspective view of yet another embodiment of a support frame member having three fingers.

In yet another embodiment of the present invention as shown in FIG. 41, the replacement pad 300, and in particular EAM pad 200, is supported by a support frame member 229 having a several fingers 432 oriented in the z-direction about vertical axis 410. For instance, in the embodiment shown, there are three fingers 432. Most desirably, fingers 432 have the ability to flex so that when the EAM pad 200 is inserted into ear canal 26, the fingers 432 can more easily deform to fit the contours of the ear canal.

Still referring to FIG. 41, each finger 432 has a distal portion 438 and an opposite base portion 434 extending from a platform 436. Further, each finger has a longitudinal axis or at least a segment thereof that is aligned with a longitudinal axis. Generally, these longitudinal axes and segments are parallel to one another. Each finger 432 may be arranged in a circle about the vertical axis 410 having a diameter defined by the outer surface 440 of each finger 432. The distal portion 438 may have a reduced diameter as compared to the base portion in order to follow the contour of the outer surface 428 of an EAM pad 200 and to increase flexibility at the distal portion. In the alternative, the fingers 432 may have a constant diameter between the base portion and the distal portion.

It is noted at this point that the ear canal 26 does not have a perfect cylindrical cross-section. To the contrary, a cross section of a typical ear canal 26, anywhere along its length may more resemble an oval cross-section. When using highly conformable materials, the fact that an EAM pad 200 may be circular can be of little consequence. However, some of the support frames 229 which are used to support the EAM pad 200 may be less flexible than others, and may benefit from having an oval configuration to better match a typical ear canal 26. Thus, it may be desirable in some embodiments to provide an EAM pad support 412 having an oval cross-section as described below.

Figure 29B:
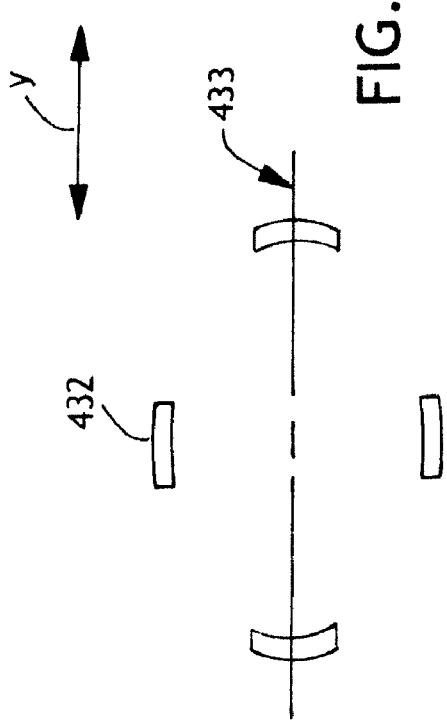
FIG. 29B is a plan view of the top surfaces of the support frame fingers shown in FIG. 29A.
Figure 29C:
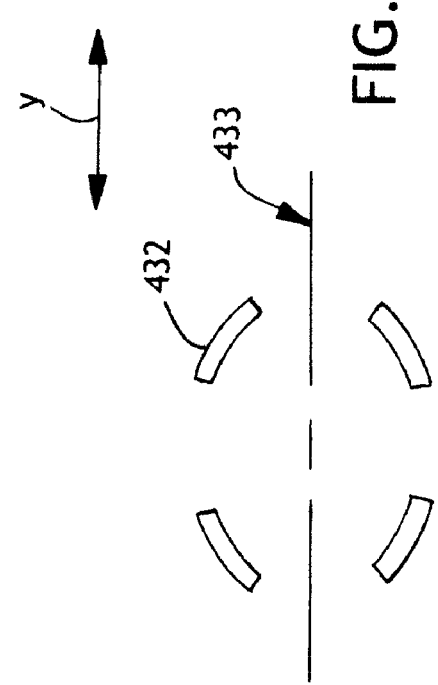
FIG. 29C is a plan view of an alternative finger arrangement with respect to the axis shown in FIG. 29A.
Figure 29A:
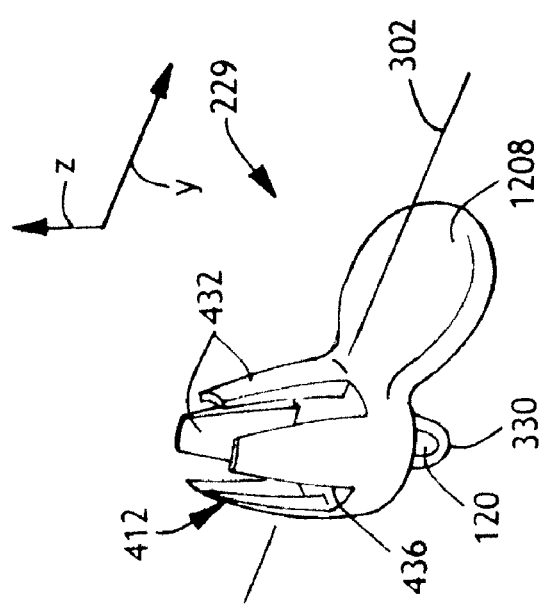
FIG. 29A is a perspective view of alternative embodiment of a support frame member having a plurality of fingers.
Figure 32:
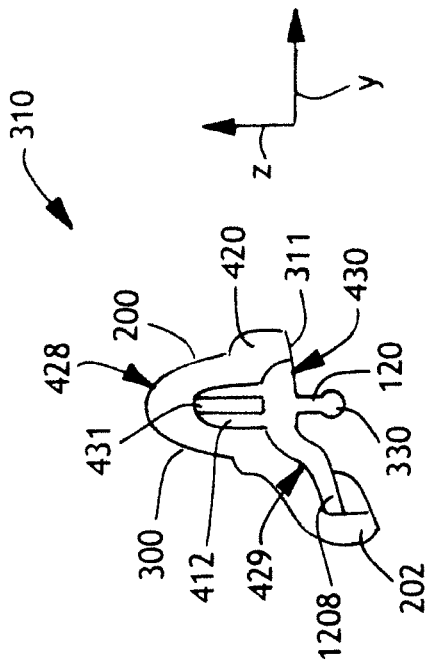
FIG. 32 is front perspective view of a twelfth embodiment of a hearing protector of the present invention (left-side version).

Thus, referring to FIGS. 29 (*a-c*), there may be four fingers 432 may be arranged in a circle as described in the prior embodiment, or arranged into an oval shape. The longitudinal axis 433 of the oval is aligned with the longitudinal axis 302 of the replacement assembly 310 as viewed in the x-y plane (see FIGS. 29*c* and 38). This allows fingers 432 to collapse about the axis of symmetry and conform to any irregularity of an ear canal 26.

It may be desirable to arrange the fingers 432 such that the axis 433 does not intersect a portion of a finger 432, as shown in FIG. 29B. Most desirably, the axis 433 falls anywhere within the space between each finger 432, and may be directly adjacent to a finger 432.

As mentioned, replacement assembly 310 may be selectively removed and replaced with a new or different replacement assembly 310. Though not required, it is desirable to have a stem head 330 and replacement assembly 310 that will fit in either a right- or left-sided ear clip. This can simplify merchandise inventory, reduce product costs, and make it more convenient users to replace a replacement assembly. The "positioning member" is defined as any structure that a wearer touches to position the hearing protector 100 within the ear. Most desirably, such structures are rigid or semi-rigid and may include a handle 100, a neck 104, a shoulder 106, a bow 108, and a pressure bearing member 205. Other structures may be used as a positioning member even if they are relatively compliant. For example, flange 420 may operate as a positioning member provided that it is large enough to grasp effectively.

Figure 26A:
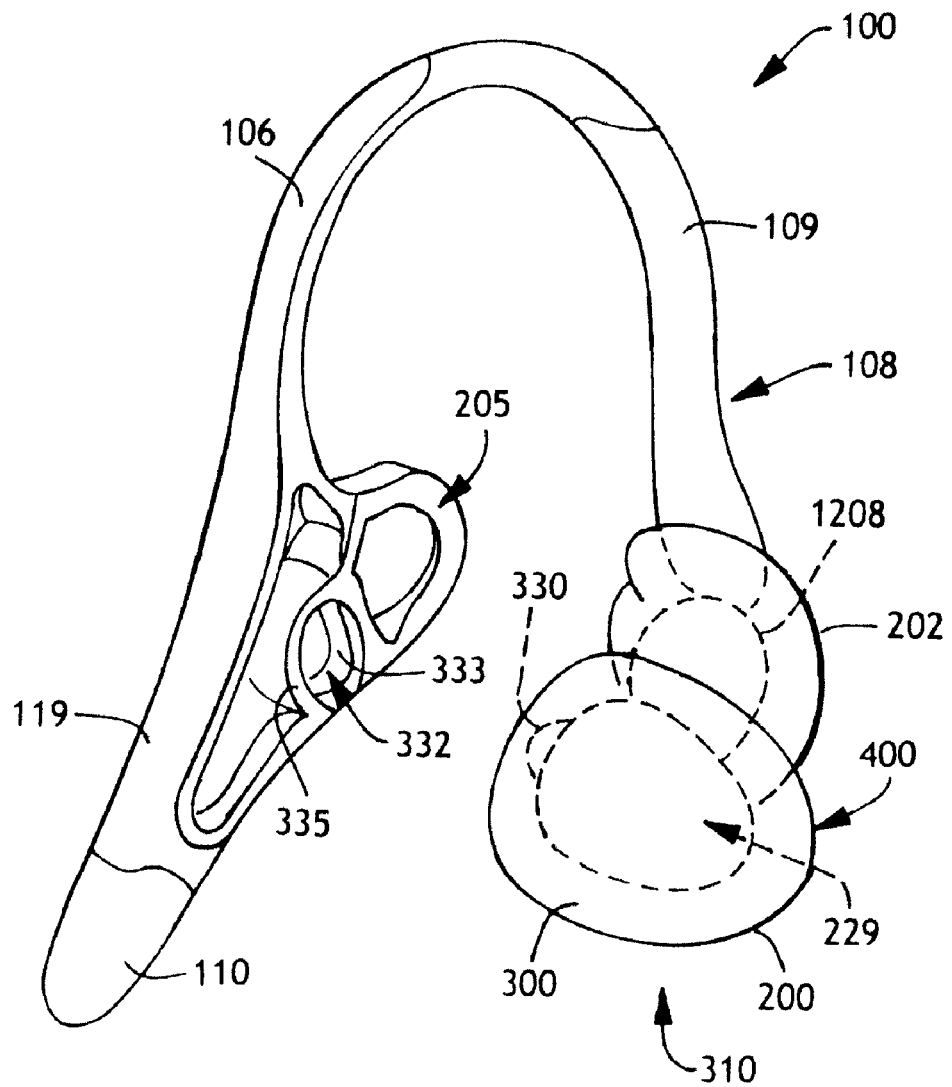
FIG. 26A is partially exploded view of an eleventh embodiment of a right-side version of a hearing protector of the present invention.
Figure 26B:
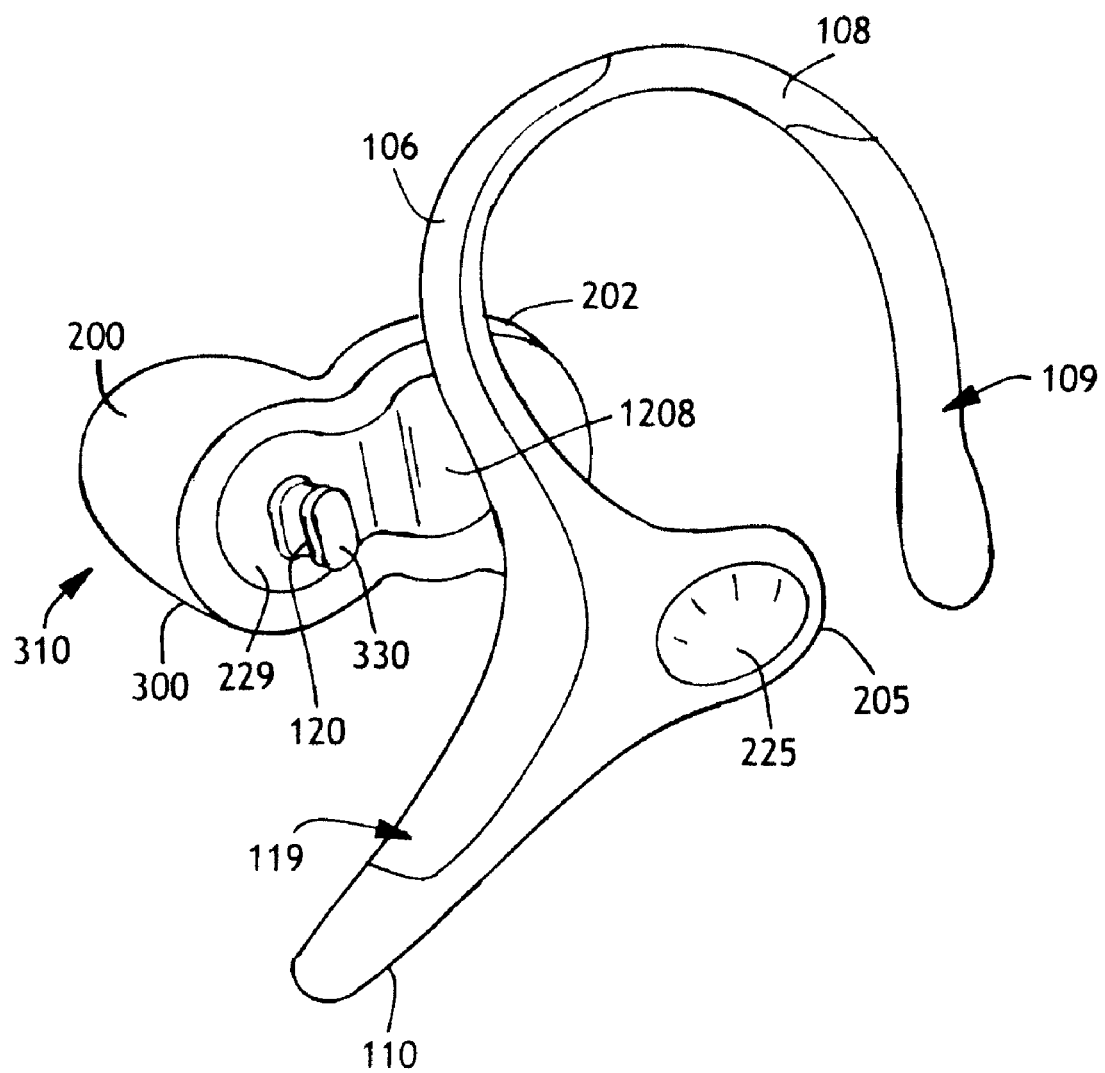
FIG. 26B is partially exploded view of the hearing protector of FIG. 26A, shown from an opposite direction.

Referring now to FIGS. 26A and 26B, exploded views show one embodiment of how a separate frame member 229 can be selectively or non-selectively attached to an ear clip. As previously discussed, a stem may be attached to a cavity by friction or interference fit. In one embodiment, the stem 120 may be configured in such a way that rotation between the replacement assembly 310 and the ear clip cannot occur (see FIG. 26B). For example, the stem 120 may have an elongated stem head 330 that coincides with an elongated cavity 332 (see FIG. 26A). Because of the elongated shape, no rotation can occur between the stem head 330 and cavity 332. Inside cavity 332 is a ridge 333 that may surround the entire inner wall 335 defining cavity 332. When the stem head 330 is forced beyond this ridge, the replacement assembly stays in place via an interference fit, otherwise referred to as a "snap fit." The snap fit allows a user to easily change or interchange between different shapes and types of replacement assemblies 310. Of course, other shapes could serve this same function. For example, a triangular, oval, or irregular-shaped stem head 330 and corresponding cavity 332 would function to prevent rotation. Other connections may be used as well, such as a hook and loop, adhesives, a slide mechanism, a snap, and the like.

Referring to FIGS. 26A and 26B, it can be seen that surrounding the cavity 332 is an optional handle 110, extending from one side, and a pressure bearing member 205 with optional detent 225. The pressure bearing member 205 with optional detent 225 is configured to apply pressure to the support frame member 229 primarily through the stem 120 in order that it can be used to transfer force toward the ear from the pressure plate 1208 and pressure pad 202. Of course, it is contemplated the cavity 332 may be instead placed on the replacement assembly 310, and the stem 120/head 330 on the ear clip, similar to the embodiment of FIG. 20.

Figure 44:
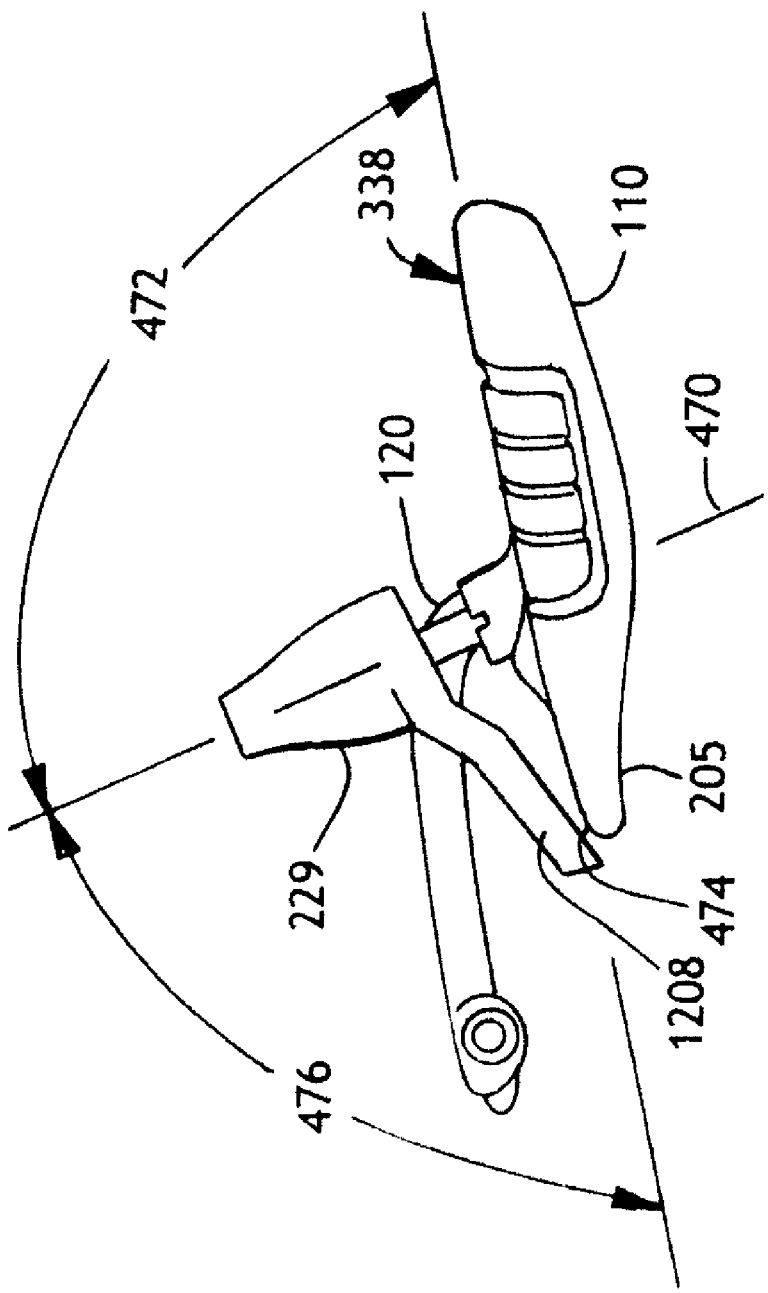
FIG. 44 is a side elevation of another embodiment of a support frame member having a fixed angle with respect to the ear clip.
Figure 46:
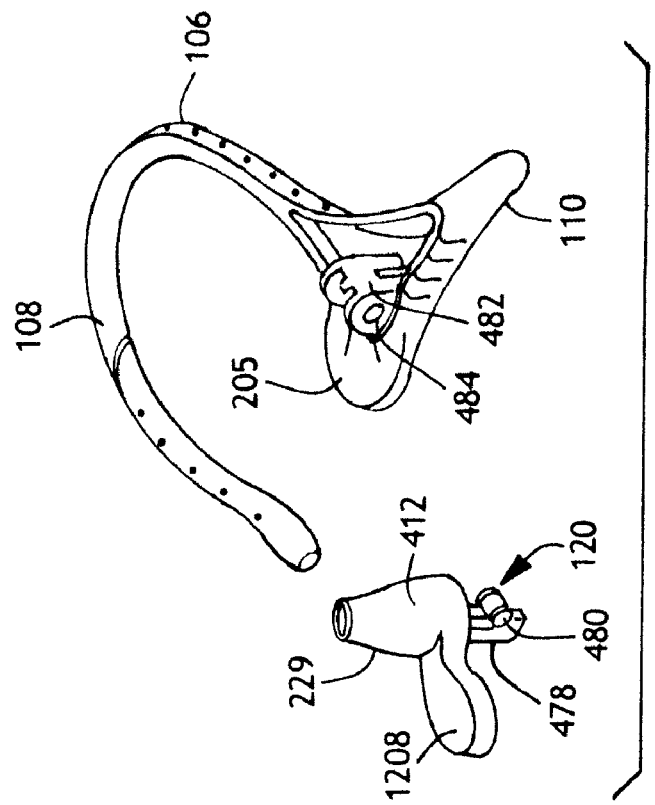
FIG. 46 a perspective view of the support frame member shown in FIG. 45.
Figure 45:
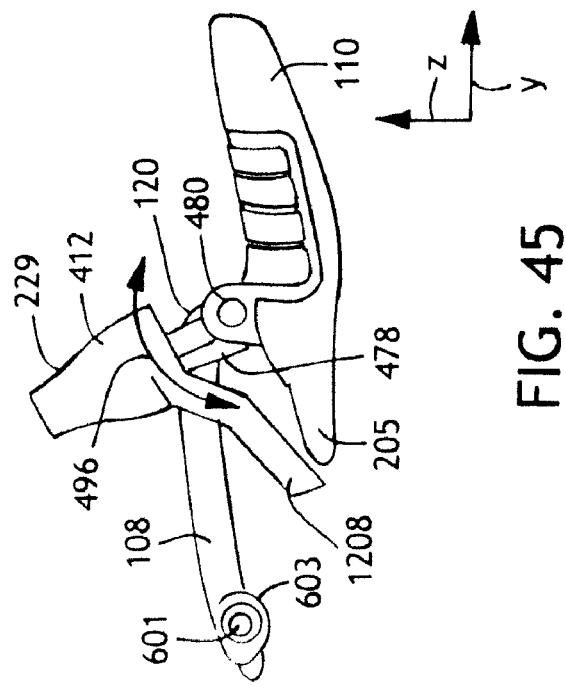
FIG. 45 is a side elevation of a further embodiment of a support frame member having a pivotal attachment with respect to the ear clip.

Referring to FIG. 44, there is yet another embodiment of a support frame member 229 and ear clip, wherein the EAM pad support frame member 229 has a longitudinal axis 470 fixed at a particular angle 472 with respect to the inside handle surface 338 of the handle 110. (The replacement pad 300 and the overlays 109 and 119 are merely omitted for simplicity or illustration). Angle 472 may be about 75 degrees to about 160 degrees, and desirably, the angle 472 may be about 105 degrees to about 140 degrees. However, the fixed angle could instead be measured from the outer plate surface 474 of the pressure bearing member 205. In this case, the angle 476 would be about 20 to about 105 degrees, and desirably, about 40 to about 75 degrees. The stem 120 may be permanently fixed or removably attached to the ear clip neck 104. Referring now to FIGS. 45-46, there is a further embodiment of a support frame member 229 and ear clip, wherein the support frame member 229 has a pivotal attachment to the ear clip. (The replacement pad 300 and the overlays 109 and 119 are merely omitted for simplicity or illustration). The stem 120 has a support 478. Support 478 has opposite sides from which a pins 480 extend. The support 478 fits within a bracket 482, and pins 480 snap into apertures 484 on each side of the bracket to form a hinge. When assembled as shown in FIG. 45, the support frame member 229 is free to rotate in direction 496 about the longitudinal axis of the pins located in the z-y plane. The replacement assembly may be easily removed and replaced by snap-fitting the pins 480 onto the apertures 484.

Figures 47, 48:
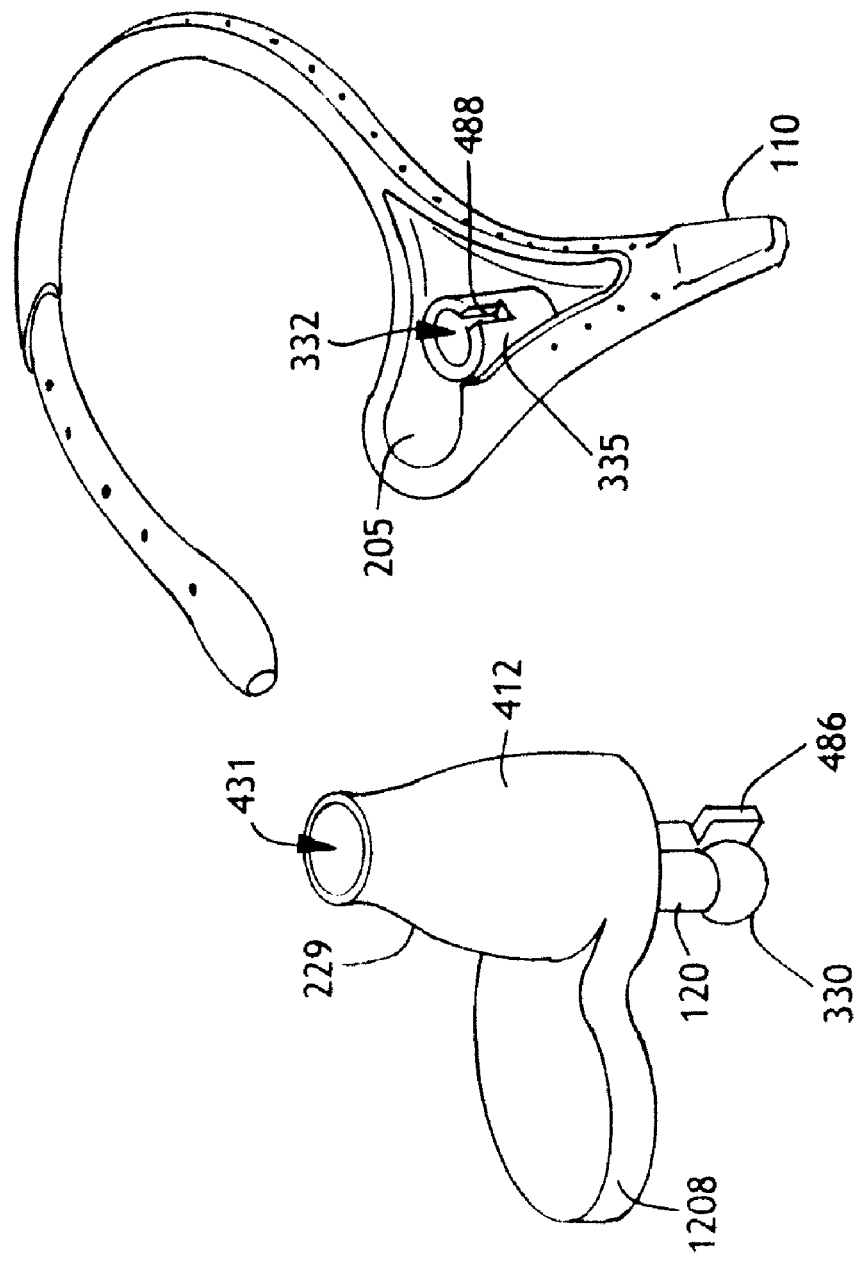
FIG. 47 is a perspective view of yet another embodiment of a support frame member having a boss extending from the stem and head.
FIG. 48 is a perspective view of an ear clip having a socket with a slot for receiving the boss of FIG. 47.

Referring now to FIGS. 47 and 48, there is a further embodiment of a support frame member 229 and ear clip, wherein the support frame member 229 has a boss 486 extending from the stem 120 and/or stem head 330 to prevent the user from placing the replacement assembly 310 onto the ear clip in the wrong direction. (The replacement pad 300 and the overlays 109 and 119 are merely omitted for simplicity or illustration). In particular, boss 486 may be a rectangular member aligned with the longitudinal axis of the stem 120. A slot 488 is placed in the wall 335 defining cavity 332. The only way the stem head 330 can be snap fitted into the cavity 332 is by properly aligning the boss 486 with the slot 488. It is contemplated that other boss shapes are possible, and the boss should not be limited to a rectangular shape. The boss may be any protrusion or multiple protrusions that would fit into slot 488 and prevent the incorrect orientation of the support frame member 229 with respect to the ear clip.

The embodiments shown in FIGS. 44-48 may be adapted to any of the embodiments shown in FIGS. 26-43, as well as prior embodiments such as that shown in FIG. 20.

As with prior embodiments of the present invention, optional touch indicia may be located on the optional handle 110 and/or bow member 108 and serve to indicate where the user should touch the hearing protector 100 for the positioning thereof. The touch indicia may be defined by a different material, color, texture, and/or symbols. For example, the detent 225 and overlays 109 and 119 define touch indicia for the embodiment shown in FIG. 20. Touch indicia may look and/or feel different to the user.

Figure 42A:
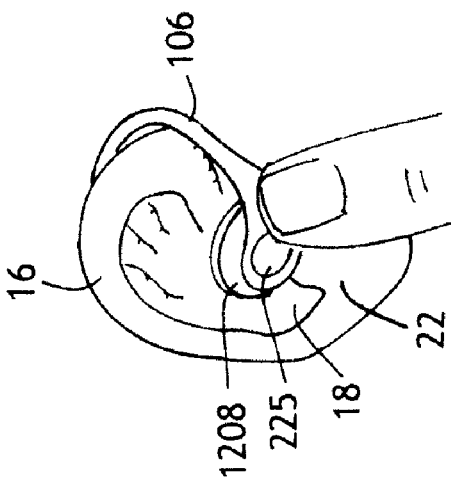
FIGS. 42 A-D shows a four-step demonstration of how any of the embodiments of FIGS. 26-41 may be inserted into a users ear.
Figure 42B:
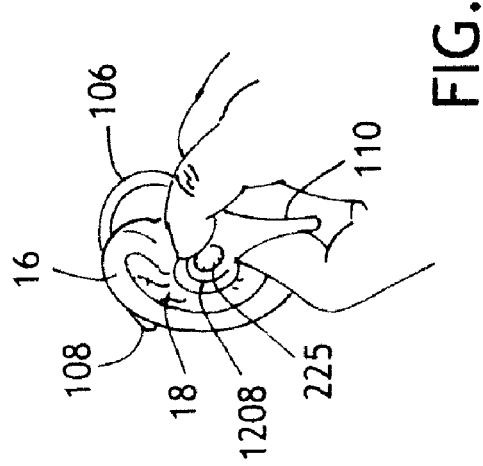
Figure 42C:
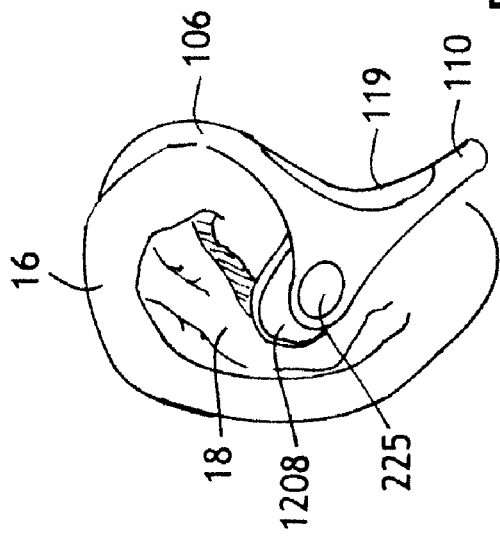

In operation, the hearing protection device of FIGS. 26-41 may be used as follows. First, as seen in FIG. 42(a), the user loops the ear clip around the pinna portion of the ear. Referring next to FIG. 42(b), as the user pulls the pinna toward the top of the user's head, the EAM pad 200 is inserted into the ear canal and the pressure pad 202 is wedged between the antitragus 22 and the concha 24 regions of the ear. Referring to FIG. 42(c), the user may push on the ear clip to in turn push the EAM pad 200 toward the ear canal for about 30 seconds as the EAM pad 200 and the pressure pad 202 expand or otherwise conform to the ear. Desirably, indicia such as the detent 225 or another tactilely detectable feature will guide and allow users to push on the best part of the hearing device for placement. It is contemplated that the indicia could instead or include a different texture. Further, the indicia may be different in color, even though this will not aid with tactile differentiation.

Figure 42D:
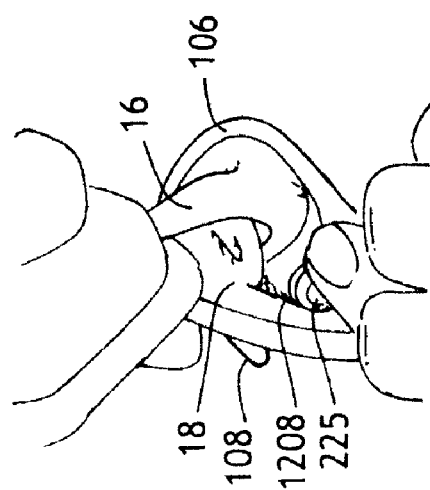
Figure 43C:
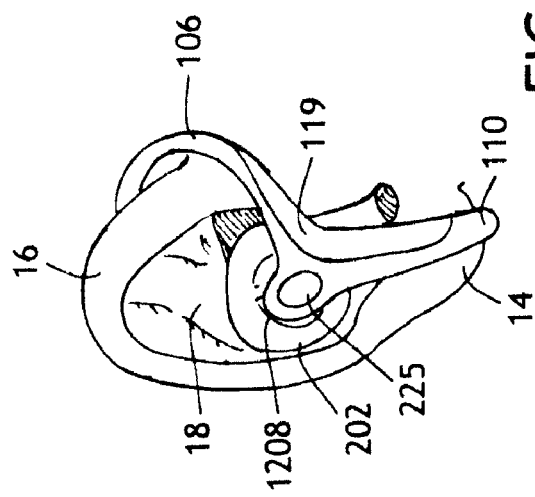
FIGS. 43 A-D illustrates how any of the embodiments of FIGS. 26-41 may appear when inserted fully or partially.
Figure 43D:
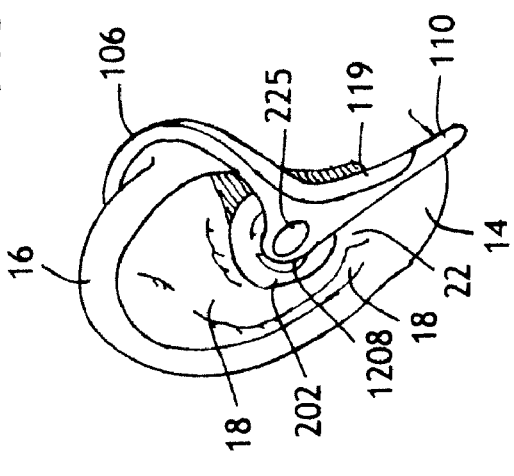
Figure 43A:
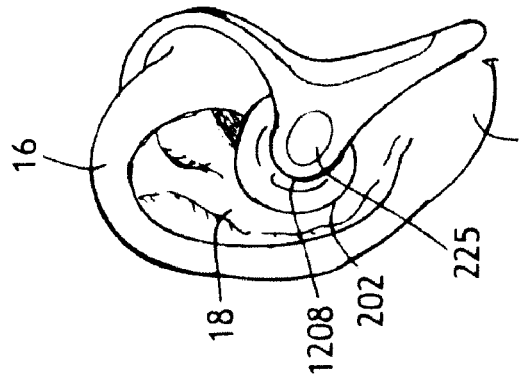
Figure 43B:
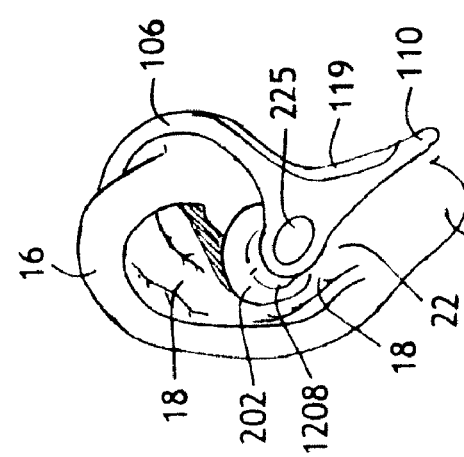

In use, the pressure pad 202 stays tucked against back concha 11 region of the concha 24 as seen in FIG. 42(d). It will be apparent when the hearing device 100 is not properly placed because the handle 110 will appear to be displaced, relative to the condition when the hearing device 100 is properly fitted to the ear. The abnormal displacement of the handle may signal to a user or independent observer such as a co-worker or supervisor, that the ear clip hearing protector 100 is not properly in place. FIG. 43 (a and c) demonstrate how a user can move the handle 110 away from the face to dislodge the EAM pad 200 from the ear canal 26. This may be desirable when the user temporarily desires to reduce the effectiveness of the EAM pad 200. Further, when the handle appears to be misplaced on a person, it will alert safety personnel to remind the user to readjust the hearing protection device for maximum protection. The correct position for optimal attenuation is shown in FIGS. 43 (b and d).

Although only a few exemplary embodiments of this invention have been described in detail above, those skilled in the art will readily appreciate that many modifications are possible in the exemplary embodiments without materially departing from the novel teachings and advantages of this invention. For example, any of the embodiments of the present invention may be adapted for use as an ear phone (not shown). As one skilled in the art of ear phone technology will realize, electronics for transmitting sound may be embedded in the ear clip and attached to speaker located in the neck 104. The plug member 102/EAM pad 200 may at least partially cover the speaker. In addition, it should be understood that the various features of each of the embodiments may be combined, and that the claims should not be limited to read upon the few examples shown and described herein.

As used herein the terms "connected" and "attached" refer to the condition where a first member or component is either mechanically and/or chemically joined to a second member or component. The term "integral" refers to a special joining between two components that occurs as a result of a permanent connection at a chemical level, e.g. a weld or two parts that were injection molded at the same time without subsequent separation. The term "passive" refers to the ability to attenuate sound without the use of noise-cancellation electronics to a level of 10 decibels or greater, or more desirably to a level of 15 decibels or greater.

When introducing elements of the invention or the preferred aspect(s) thereof, the articles "a", "an", "the" and "said" are intended to mean that there are one or more of the elements. The terms "comprising," "including," and "having" are intended to be inclusive and mean that there may be additional elements other than the listed elements.

We claim:

1. A hearing protection device for the passive attenuation of sound at a single human ear canal, the device comprising:
   a first replacement assembly comprising an EAM pad that is integrally connected to a pressure pad, wherein the pressure pad fits into a cavum conchae region of the human ear, and a support frame; and
   a positioning member that assists with disposing at least a portion of the EAM into the ear canal, the positioning member defined by an ear clip comprising a neck, a shoulder, and an arm.

2. The hearing protection device of claim 1 further comprising a handle that extends from the shoulder or the neck, wherein the handle does not have a cord member attached thereto.

3. The hearing protection device of claim 1 wherein the first replacement assembly is attached to the positioning member by a hinge.

4. The hearing protection device of claim 1 wherein the first replacement assembly is attached to the positioning member at a fixed angle.

5. The hearing protection device of claim 1 further comprising a stem extending from the first replacement assembly for selectively attaching the positioning member to the first replacement assembly.

6. The hearing protection device of claim 1 further comprising a stem having a stem head, and a boss extending from the stem or stem head, wherein the boss is adapted to engage a slot located in a cavity, and wherein the stem is located on one of the positioning member or the first replacement assembly, and the cavity is located on the other of the positioning member or the first replacement assembly.

7. The hearing protection device of claim 1 wherein the support frame member comprises a plurality of fingers each having a longitudinal axis and arranged in spaced apart configuration such that at the longitudinal axes are parallel or convergent.

8. The hearing protection device of claim 7 wherein the fingers are spaced apart in an oval shape.

9. The hearing protection device of claim 1 wherein the first replacement assembly comprises an EAM pad having a domal shape.

10. The hearing protection device of claim 1 wherein the first replacement assembly comprises an EAM pad having a stepped-domal shape.

11. The hearing protection device of claim 1 wherein the first replacement assembly comprises an EAM pad having a cone shape.

12. The hearing protection device of claim 1 wherein the support frame is permanently affixed to the ear clip.

13. The hearing protection device of claim 1, further comprising:
a second replacement assembly,
wherein the EAM pad of the first replacement assembly has a first configuration, and the second replacement assembly comprises an EAM pad having a different and second configuration, and wherein the first replacement assembly and the second replacement assembly are configured to be selectively attachable to the positioning member.

14. The hearing protection device of claim 13 further comprising a third replacement assembly having an EAM pad with a different and third configuration.

15. The hearing protection device of claim 13 wherein the first and second replacement assemblies further comprise an anti-rotation stem for connection to the positioning member.

16. The hearing protection device of claim 13 wherein the first and second replacement assemblies differ with respect to the EAM pad length.

17. The hearing protection device of claim 13 wherein the first and second replacement assemblies differ with respect to the EAM pad shape.

18. The hearing protection device of claim 13 wherein the second replacement assembly is connected to the positioning member by a temporary connection selected from the group consisting of: a ball and socket, and a hinge.

19. A hearing protection device adapted to fit a human ear canal comprising:
a plug member, wherein the plug member passively attenuates sound and is attached to a positioning member, the positioning member being defined by an ear clip comprising a neck, a shoulder and an arm; and
a pressure pad that is attached to the positioning member or the plug member, wherein the pressure pad fits into a cavum conchae region of the human ear;
wherein the positioning member is adapted to make contact with an ear structure near the human ear canal to limit how far the plug member may enter into the human ear canal when the hearing protection device is positioned to effectively attenuate sound in the human ear to a desired attenuation level.

20. The passive hearing protection device of claim 19 wherein the plug member comprises an EAM pad.

21. The passive hearing protection device of claim 19 wherein the plug member and the pressure pad are part of a replacement assembly.

* * * * *